United States Patent [19]

Sinclair et al.

[11] Patent Number: 5,502,158

[45] Date of Patent: Mar. 26, 1996

[54] DEGRADABLE POLYMER COMPOSITION

[75] Inventors: Richard G. Sinclair, Columbus; Edward S. Lipinsky, Worthington, both of Ohio

[73] Assignee: Ecopol, LLC, Golden, Colo.

[21] Appl. No.: 950,854

[22] Filed: Sep. 22, 1992

Related U.S. Application Data

[63] Continuation-in-part of Ser. No. 579,000, Sep. 6, 1990, Pat. No. 5,216,050, and Ser. No. 579,005, Sep. 6, 1990, Pat. No. 5,180,765, and Ser. No. 579,460, Sep. 6, 1990, Pat. No. 5,252,642, and Ser. No. 579,465, Sep. 6, 1990, abandoned, each is a continuation-in-part of Ser. No.387,676, Jul. 31, 1989, abandoned, and Ser. No. 387,678, Jul. 31, 1989, abandoned, and Ser. No. 386,844, Jul. 31, 1989, abandoned, and Ser. No. 387,670, Jul. 31, 1989, abandoned, each is a continuation-in-part of Ser. No.229,894, Aug. 8, 1988, abandoned, and Ser. No. 229,896, Aug. 8, 1988, abandoned, and Ser. No. 317,391, Mar. 1, 1989, abandoned, and Ser. No. 229,939, Aug. 8, 1988, abandoned.

[51] Int. Cl.$^6$ .................................................. C08G 63/08
[52] U.S. Cl. ........................ 528/354; 523/124; 524/306; 524/310; 524/315; 524/317; 524/320; 528/361
[58] Field of Search ...................... 524/306, 310, 524/315, 317, 320; 528/354, 361; 523/124

[56] References Cited

U.S. PATENT DOCUMENTS

| | | | |
|---|---|---|---|
| 1,995,970 | 3/1935 | Dorough | 260/2 |
| 2,703,316 | 3/1955 | Schneider | 260/78.3 |
| 3,565,869 | 12/1968 | Deprospero | 260/78.3 |
| 3,636,956 | 1/1972 | Schneider | 128/335.5 |
| 3,755,558 | 8/1973 | Scribner | 424/17 |
| 3,773,919 | 11/1973 | Boswell et al. | 424/19 |
| 3,792,010 | 2/1974 | Wasserman et al. | 260/32.2 |
| 3,797,499 | 3/1974 | Schneider | 128/334 |
| 3,839,297 | 10/1974 | Wasserman et al. | 260/78.3 |
| 3,844,987 | 10/1974 | Clendinning et al. | 260/7.5 |
| 3,867,190 | 2/1975 | Schmitt et al. | 117/138.8 |
| 3,982,543 | 9/1976 | Schmitt et al. | 128/335.5 |
| 3,991,766 | 11/1976 | Schmitt et al. | 128/335.5 |
| 4,027,676 | 6/1977 | Mattel | 128/335.5 |
| 4,057,537 | 11/1977 | Sinclair | 260/78.3 |
| 4,137,921 | 2/1979 | Okuzumi et al. | 128/335.5 |
| 4,201,216 | 5/1980 | Mattel | 128/335.5 |
| 4,481,353 | 11/1984 | Nyilas et al. | 528/303 |
| 4,539,981 | 9/1985 | Tunc | 128/92 |
| 4,550,449 | 11/1985 | Tunc | 623/16 |
| 4,620,999 | 11/1986 | Holmes | 428/35 |
| 4,643,191 | 2/1987 | Bezwada et al. | 128/335.5 |
| 4,643,734 | 2/1987 | Lin | 623/16 |
| 4,675,189 | 6/1987 | Kent et al. | 424/490 |
| 4,828,840 | 5/1989 | Sakamoto et al. | 424/474 |
| 4,832,686 | 5/1989 | Anderson | 604/49 |
| 4,915,893 | 4/1990 | Gogolewski et al. | 264/205 |
| 4,961,707 | 10/1990 | Magnusson et al. | 433/215 |
| 4,962,091 | 10/1990 | Eppstein et al. | 514/2 |
| 5,051,272 | 9/1991 | Hermes et al. | 427/2 |
| 5,061,281 | 10/1991 | Mares et al. | 623/11 |
| 5,066,231 | 11/1991 | Oxman et al. | 433/214 |
| 5,066,772 | 11/1991 | Tang et al. | 528/354 |
| 5,076,983 | 12/1991 | Loomis et al. | 264/101 |
| 5,085,629 | 2/1992 | Goldberg et al. | 604/8 |
| 5,180,765 | 1/1993 | Sinclair | 524/306 |

FOREIGN PATENT DOCUMENTS

| | | |
|---|---|---|
| 863673 | 2/1971 | Canada . |
| 0058481 | 2/1981 | European Pat. Off. . |
| 0140255 | 10/1983 | European Pat. Off. . |
| 887535 | 10/1988 | South Africa . |
| 891718 | 3/1989 | South Africa . |
| 779291 | 1/1955 | United Kingdom . |
| 2223027 | 11/1989 | United Kingdom . |
| WO86/00533 | 7/1984 | WIPO . |
| WO88/04557 | 12/1986 | WIPO . |
| WO90/01521 | 8/1988 | WIPO . |
| WO92/01548 | 7/1990 | WIPO . |
| WO92/01737 | 7/1990 | WIPO . |
| WO92/04410 | 9/1990 | WIPO . |
| WO92/04412 | 9/1990 | WIPO . |
| WO92/05311 | 9/1990 | WIPO . |

OTHER PUBLICATIONS

Barrows, *Degradable Implant Materials: A Review of Synthetic Absorbable Polymers and Their Applications*, Clinical Materials 1986:1:233–257.

Bodemeier et al., *The Effect of Addition of Low Molecular Weight Poly(DL–Lactide) Drug Delivery Systems*, International Journal of Pharmaceutics, No. 51, 1989, Elsevier Science Publishers, B.V., p. 108.

Lipinsky et al., *Is Lactic Acid a Commodity Chemical*, Chemical Engineering Progress, Aug. 1986, pp. 26–32.

Pitt et al., *Sustained Drug Delivery Systems. I. The Permeability of Poly($\epsilon$–Caprolactone), Poly(DL–Lactic Acid), and Their Copolymers*, Journal of Biomedical Materials Research, vol. 13, pp. 497–507, John Wiley & Sons, Inc., 1979.

Sinclair, *Glycolide and Lactide Copolymers for Slow Release of Chemotherapeutic Agents*, Proceedings, Fifth International Symposium on Controlled Release of Bioactive Materials, Aug. 14–16, 1978, University of Akron.

Sinclair, *Lactic Acid Polymers–Controlled Release Applications for Biomedical Use and Pesticide Deliver*, Proceedings First Annual Corn Utilization Conference, Jun. 11 and 12, 1987, presented by National Corn Growers Association and Funk Seeds International.

Wehrenberg, *Lactic Acid Polymers: Strong, Degradable Thermoplastics*, Me, vol. 65, Sep. 1981.

(List continued on next page.)

*Primary Examiner*—Edward J. Cain
*Attorney, Agent, or Firm*—Sheridan Ross & McIntosh

[57] ABSTRACT

Disclosed are degradable materials which include a nontoxic hydrolytically degradable polymer and nontoxic modifier, wherein the modifier is compatible with the polymer and the modifier is nonvolatile and nonfugitive. Also disclosed are processes for forming the various degradable materials, which include films, molded products, laminates, foams, powders, nonwovens, adhesives and coatings. The disclosed materials and processes are particularly useful for the production of commercial and consumer products in high volumes which are suitable for recycling after use or which are discarded into the environment in large volumes.

73 Claims, No Drawings

OTHER PUBLICATIONS

Watson, *Lactic Acid Polymers as Constituents of Synthetic Resins and Coatings,* Industrial and Engineering Chemistry, vol. 40, No. 8, pp. 1393–1397, Aug. 1948.

Wise, et al., *Lactic/Glycolic acid Polymers,* Drug Carriers in Biology and Medicine, pp. 237–270, N.Y., 1979.

Wise, *Biopolymeric Controlled Release Systems,* vol. I, CRC Press, Inc., 1984.

Vert, *Biomedical Polymers from Chiral Lactides and Functional Lactones: Properties and Applications,* Makromol. Chem., Macromol. Symp. 6, pp. 109–122, 1986.

DEGRADABLE POLYMER COMPOSITION

REFERENCE TO RELATED APPLICATIONS

The present application is a continuation-in-part of U.S. patent application Ser. Nos. 07/579,000, entitled "Blends of Polylactic Acid"; 07/579,005, entitled "Biodegradable Packaging Thermoplastics from Polylactic Acid"; 07/579,460, entitled "Degradable Impact Modified Polylactic Acid"; and 07/579,465, entitled "Biodegradable Replacement of Crystal Polystyrene"; all filed on Sep. 6, 1990; which are continuation-in-parts of U.S. patent application Ser. Nos. 07/387,676; 07/387,678; 07/386,844; and 07/387,670; respectively, all filed on Jul. 31, 1989, and now abandoned; which are continuation-in-parts of U.S. patent application Ser. Nos. 07/229,894, filed Aug. 8, 1988; 07/229,896, filed Aug. 8, 1988; 07/317,391, filed Mar. 1, 1989; and 07/229,939, filed Aug. 8, 1988; respectively, now abandoned; and all of which are incorporated by reference herein in their entirety.

FIELD OF THE INVENTION

The invention relates to degradable polymer compositions and materials including those compositions.

BACKGROUND OF THE INVENTION

Some polymers are known to degrade by hydrolysis in the presence of water and thereby decompose to smaller chemical units. Some of these polymers are also biodegradable, such as polylactic acid and polyglycolic acid. Due to the expense and difficulty in preparing these hydrolytically degradable polymers, their use has been largely confined to high value medical applications where bioabsorbable materials are required. Most reported medical applications involve internal use of the polymers, such as for sutures, prosthetic devices, and drug release matrices. Some polymers that have received considerable attention for medical applications include polylactic acid, polyglycolic acid, poly-$\epsilon$-caprolactone and polydioxanone.

Medical applications, however, involve relatively predictable and constant environmental conditions to which the polymers are subjected during use, i.e., the human body. Therefore, the need to manipulate or modify the properties of polymers used in such medical applications has not been great.

Some attempts, however, have been made in the medical field to vary properties of bioabsorbable polymers based on the specific intended use. Properties that have received some attention include strength, flexibility, and rate of hydrolytic degradation. It is generally known that a copolymer usually exhibits different properties than homopolymers of either individual comonomer. Some attempts have been made to develop specific copolymers for specific medical applications.

For example, various copolymers containing lactic acid repeating units and glycolic acid repeating units have been suggested for various uses. For example, U.S. Pat. No. 3,867,190 by Schmitt et al., issued Feb. 18, 1975, discusses medical uses for a copolymer containing, by mole percent, from about 15 to 85% glycolic acid and from about 85 to 15% lactic acid. U.K. Patent Application Publication No. 2223027A by Ikada et al., published Mar. 28, 1990, discusses the use of lactide/glycolide copolymers for regenerative treatment of the periodontium.

Medical uses for copolymers containing $\epsilon$-caprolactone and lactide have also been suggested. U.K. Patent Application Publication No. 2223027A also discusses the use of a lactide/$\epsilon$-caprolactone copolymer, also for regenerative treatment of the periodontium. U.S. Pat. No. 4,643,734 by Lin, issued Feb. 17, 1987, discusses composite surgical articles made from carbon fibers and lactide/$\epsilon$-caprolactone copolymers. Preferably, the copolymer contains from about 60 to about 95 weight percent $\epsilon$-caprolactone. The resulting composite is reported to not be stiff.

U.S. Pat. No. 5,085,629 by Goldberg et al., issued Feb. 4, 1992, discusses a terpolymer of L-lactide, glycolide and $\epsilon$-caprolactone for use as a biocompatible, biodegradable, resorbable infusion stent composed of from about 15 to about 25 weight percent $\epsilon$-caprolactone, from about 45 to about 85 weight percent L-lactide, and from about 5 to about 50 weight percent glycolide. It is stated that the controlling factor in the stiffness of the terpolymer composition is the relative amount of $\epsilon$-caprolactone monomer.

U.S. Pat. No. 4,643,191 by Bezwada et al., issued Feb. 17, 1987, discusses a crystalline copolymer produced by first polymerizing p-dioxanone to form a mixture of monomer and homopolymer, and then adding lactide to this mixture and polymerizing to form a copolymer. The polymers discussed are useful for the manufacture of surgical devices, and in particular, absorbable monofilament sutures and ligatures and hemostatic ligating clips. The polymers are reported to be more pliable than p-dioxanone homopolymers.

In addition to glycolide and $\epsilon$-caprolactone, several other comonomers have been reported for possible polymerization with lactic acid or lactide. U.S. Pat. No. 3,636,956 by Schneider, issued Jan. 25, 1972, discusses absorbable sutures prepared by extrusion of a polylactide polymer, including copolymers containing up to about 15 percent by weight of specific comonomer repeating units. Specific examples show polymerization of L-lactide with each of 5% $\beta$-propiolactone, 5% $\beta$-butyrolactone, 5% pivalolactone, 11.6% intermolecular cyclic ester of $\alpha$-hydroxybutyric acid, and 10% intermolecular cyclic ester of $\alpha$-hydroxyheptanoic acid. U.S. Pat. No. 4,481,353 by Nyilas et al., issued Nov. 6, 1984, discusses bioresorbable polyesters that are useful in making surgical articles. The polyesters are composed of a Krebs Cycle dicarboxylic acid or isomer or anhydride thereof, a diol having 2, 4, 6, or 8 carbon atoms, and an alphahydroxycarboxylic acid, which can be glycolic acid, L-lactic acid, D-lactic acid, or racemic lactic acid. U.S. Pat. No. 5,066,772 by Tang et al., issued Nov. 19, 1991, discusses bioabsorbable copolymers containing carbonate repeating units and 2-hydroxycarboxylic acid repeating ester units useful for fabricating medical devices. It is reported that, by selection and placement of monomeric units in the polymeric chain, as well as other variables, various properties of the copolymer can be tailored for various medical applications.

Many references, however, list several possible comonomers without any consideration for the possible effects that such comonomers might have on properties of the copolymer. For example, U.S. Pat. No. 2,703,316 by Schneider, issued Mar. 1, 1955, discusses lactide polymers and copolymers with up to 50% of another polymerizable cyclic ester having a 6- to 8-membered ring, capable of being formed into a tough, orientable, self-supporting thin film. The patent specifically discloses polymerization of 5 parts lactide and 5 parts glycolide and also polymerization of 12 parts lactide and 2 parts tetramethylglycolide, but also provides an extensive list of other possible comonomers with no elaboration on polymer properties.

A few references have suggested the use of hydrolytically degradable polymers outside of the medical field. For example, U.S. Pat. No. 4,057,537 by Sinclair, issued Nov. 8, 1977, discusses copolymers of L-lactide and ε-caprolactone prepared from a mixture of comonomers containing from about 50 to about 97 weight percent L-lactide and the remainder ε-caprolactone. Strength and elasticity are shown to vary depending on the relative amounts of L-lactide and ε-caprolactone monomers. Depending upon the L-lactide/ε-caprolactone ratio, the polymers are disclosed to be useful for the manufacture of films, fibers, moldings, and laminates. However, no specific applications are discussed. Sinclair discloses that plasticizers may be added to the copolymer if desired, but provides no guidance concerning what compounds might be suitable.

Although it has been noted that suitable compounds, such as plasticizers, may be added to modify the properties of some hydrolytically degradable polymers, such as in U.S. Pat. No. 4,057,537 just discussed, little guidance has been given as to what compounds might be effective. Identifying suitable compounds for use in modifying the properties of biodegradable polymers has been a major problem confronted in developing biodegradable polymers for mass-marketed products. Relatively few references discuss modification of properties of hydrolytically degradable polymers with external compounds, such as polylactide homopolymers and copolymers. The medical industry has generally sought to tailor polymer compositions to specific medical applications by developing specific copolymers, rather than to add external compounds. Those references that do discuss compounds, such as plasticizers, however, offer little guidance in selecting suitable compounds to be used for mass-marketed, hydrolytically degradable polymer products.

Compounds which effectively modify properties of polymer products are not to be confused with compounds that are designed only to aid polymer processing and that are removed prior to or during manufacture of the final product. Compounds which are effective to modify properties of polymer products should be completely miscible with the polymer, nonvolatile, and should not migrate to the surface of the polymer composition, as might be desirable with a processing aid designed to increase lubrication, as noted.

The use of plasticizers or other compounds to modify properties in mass-marketed products, such as packaging films and containers, presents several problems that are not apparent with nondegradable polymers or with hydrolytically degradable polymers used in specialty markets, such as for medical applications. Plasticizers or other similar compounds used in mass-marketed products made of hydrolytically degradable polymers will be deposited into the environment in large quantities upon degradation of the polymers. Therefore even low levels of toxicity are a concern due to the potentially huge quantity of potential waste. Toxicity is not as big of a problem with nondegradable polymers because plasticizers remain largely locked inside the polymer composition. Toxicity is not a major problem with medical applications which result in relatively little environmental contamination because the market is so much smaller. Also, low toxicity plasticizers in medical applications are present in such small quantities and are released at such slow rates such that there is reduced potential for toxicological problems. The prior art is not informative, however, concerning the use of plasticizers with hydrolytically degradable polymers, and particularly with biodegradable polymers. As noted, medical industries have tended to attempt development of specific copolymers for different medical applications. Those references that do discuss plasticization of hydrolytically degradable polymers using external plasticizers offer little insight into the special problems, as noted, concerning plasticization of mass-marketed degradable polymer compositions. Because of the potential cost advantages over specifically designed copolymers alone and because of the wide flexibility offered by effective plasticizers, a great need exists for suitable plasticized hydrolytically degradable polymer compositions.

Many of the references discussing "plasticizing" additives for hydrolytically degradable polymers to soften the composition are, in effect, processing aids that are either not present in the final product, or if present, are not incorporated into the product to provide effective plasticization. For example, U.S. Pat. No. 3,982,543 by Schmitt et al., issued Sep. 28, 1976, discusses lactic acid/glycolic acid copolymers and notes that solvents such as chloroform, xylene, and toluene soften the copolymer to obtain more sponge-like, woven, braided or felted surgical elements. Such solvents, however, are volatile compounds that aid processing, but that are not necessarily present as plasticizers in the final product.

Other processing aids even if not completely removed prior to formation of the final product, are not present in the product in a plasticizing role. U.S. Pat. No. 4,915,893 by Gogolewski et al., issued Apr. 10, 1990, discusses the use of additives to aid processing in the manufacture of biodegradable filaments, such as lactide/glycolide copolymer filaments. The additives allow the polymer to be more highly fibrillated during spinning than would be possible without the additives. The preferred additive is reported to be polyurethane which appears to be intended as a lubricant that aids spinning, but that is not completely removed from the final product. Other additives, such as glycolide, lactide, camphor, benzoic acid-2-hydroxyacetate, hexamethylbenzene, and 1,2-cyclohexanedione, however, are also discussed which do appear to be completely removed prior to finalizing the product under processing conditions disclosed therein. One example showing camphor as an additive discloses process conditions that would remove the additive during processing such that no additive was present in the final product. Also, many of the components, such as those disclosed by Schmitt et al. and Gogolewski et al., would present toxicity problems if present in a final degradable polymer composition.

The need for effective plasticized hydrolytically degradable compositions for mass-marketed products has not been adequately addressed in the prior art. The medical industry has focused on narrow applications, preferring to develop specific unplasticized copolymer compositions, and has not addressed the particular problems confronting mass-marketed products. A need exists for degradable polymer compositions that are suitable for use with mass-marketed products that can replace existing non-degradable products that are rapidly becoming difficult to dispose of due to limited landfill space and other environmental concerns.

SUMMARY OF THE INVENTION

The present invention is directed toward various degradable materials which include a nontoxic hydrolytically degradable polymer and a nontoxic modifier. The modifier is compatible with polymer and is nonvolatile and nonfugitive. The various materials of the present invention, include films, molded products, laminates, foams, powders, nonwovens, adhesives and coatings. The degradable polymer of the present materials is typically hydrolytically degradable, such as polylactic acid. The polymer and modifier are compatible with each other and typically have solubility parameters which are within about 1.0 calories per cubic centimeter of each other and the solubility parameters are typically between about 7.5 and about 16.5 calories per cubic centimeter. The modifier is nonvolatile and typically has a vapor pressure of less than about 50 Torr at 180° C. and a boiling temperature above about 280° C. at 1 atmosphere.

The present invention is also directed toward processes for making the various degradable materials of the present invention. The processes include forming a composition which includes a nontoxic hydrolytically degradable polymer and a nontoxic modifier, wherein the modifier is compatible with the polymer, into the various materials of the present invention under conditions such that the modifier is substantially nonvolatile and nonfugitive.

DETAILED DESCRIPTION OF THE INVENTION

The present invention is directed toward various materials which include a nontoxic degradable polymer and a nontoxic modifier which is compatible with the polymer and which is nonvolatile and nonfugitive. While the composition is degradable, it is typically stable for a time sufficient to make it useful for a wide variety of commercial applications. The various materials include films, molded products, laminates, foams, nonwovens, adhesives and coatings.

As used herein, the term "degradable," with reference to the various materials of the present invention refers to a material including a degradable polymer as described below and in the proportions described below. The term "degradable," with reference to the polymer, refers to a polymer having a polymer molecular structure which can decompose to smaller molecules. Such degradation or decomposition can be by various chemical mechanisms. For example, as discussed below, the degradable polymer can be hydrolytically degradable in which water reacts with the polymer to form two or more molecules from the polymer.

The polymer of the present materials is further characterized as being degradable within a time frame in which products made from the materials, after use, can either be readily recycled by decomposition of the polymer or, if disposed of in the environment, such as in landfills, the polymer degrades quickly enough to avoid significant accumulation of discarded products or wherein the rate of accumulation is significantly less than that of similar products which are not degradable.

The degradation characteristics of the polymer in the present materials depend in large part on the type of material being made with the polymer. Thus, the polymer needs to have suitable degradation characteristics so that when processed and produced into a final material, the material does not undergo significant degradation until after the useful life of the material. Therefore, different embodiments of the present invention will have different degradation characteristics. The timing of degradation of the materials can be evaluated by accelerated short-term testing under which materials are exposed to harsh conditions. For example, a useful test for degradation is an accelerated short-term test in which materials are subjected to a temperature of 95° F. (35° C.) and 95% humidity. Under these conditions, for purposes herein, a test sample of material which is in the configuration of a 1–3 mil film is considered to be degradable if it becomes sticky to the touch, cloudy or opaque and embrittled in less than about three months. Under these same conditions, for purposes herein, a test sample of material which is in the configuration of a 1–3 mil film is considered to be degradable if it has a tensile strength loss of at least about 90% in less than about six months.

The polymer of the present invention can be characterized as being hydrolytically degradable. As used herein, the term "hydrolytically degradable" refers to a composition in which chemical bonds in the molecule are subject to hydrolysis, thus producing smaller molecules. In a further embodiment of the present invention, the polymer is biodegradable. Biodegradability refers to a compound which is subject to enzymatic decomposition, such as by microorganisms, or a compound, portions of which are subject to enzymatic decomposition, such as by microorganisms. In one instance, for example, a polymer such as polylactic acid can be degraded by hydrolysis to individual lactic acid molecules which are subject to enzymatic decomposition by a wide variety of microorganisms.

Hydrolytic degradation rates for various materials of the present invention, can be controlled in a number of ways. Various degradation strategies are discussed in detail in copending, commonly assigned U.S. patent entitled "Degradation Control of Environmentally Degradable Disposable Materials" (Attorney File No. 4042-29), which is incorporated herein by reference in its entirety. One method of controlling the rate of hydrolytic degradation of the materials is to control acid or base catalyzed degradation of the polymer. While not being bound by theory, it is believed that polymers of hydroxycarboxylic acids degrade by two mechanisms: random scission within the polymer and end-biting of the terminal hydroxyl ends of the polymer. In addition, the carboxyl ends apparently promote degradation both by polarizing ester bonds and by providing acid groups that increase (i.e., accelerate) the rate of hydrolysis as it is believed that free carboxyl groups are surrounded by shells of water which promote degradation. As more carboxyl end groups are formed during hydrolysis, there are additional acid groups which trap and accumulate water. It is further believed that while reactive hydroxyl ends may be more responsible for enhancing degradation during melt processing, free carboxyl ends are more responsible for degradation during use and disposal stages of a product's life. Thus, in one embodiment, by esterifying the terminal carboxyl group with an end-capping agent, such as for example ethanol, catalysis of hydrolytic degradation can be reduced. Additionally, end-capping of the terminal hydroxyl groups reduces degradation.

Additionally, other strategies can be used to control degradation based on acid or base catalysis of degradation. For example, materials can be produced which include encapsulated acid or base compounds which, upon release, rapidly promote degradation. For example, acid or base compounds can be encapsulated in degradable polymeric material or abrasion prone material so that subsequent to use and being discarded, the capsules will breakdown and release acid or base compounds to speed degradation of the entire material.

A further strategy for controlling degradation of materials of the present invention is to change the molecular weight of the polymer. Higher molecular weight material will degrade more slowly because each polymeric molecule requires more hydrolytic reactions for total degradation. Higher molecular weights of polylactic acid can be achieved, for example, by polymerizing lactide, rather than direct polymerization of lactic acid. Other polymerization techniques for achieving high molecular weights are well known. In addition, cross-linking of polymers achieves effective higher molecular weights and more tightly bound materials which degrade at a slower rate.

A further mechanism for controlling the rate of degradation of materials of the present invention is to change the hydrophobic or hydrophilic nature of the material. The degradation rate of a polymer that is hydrolytically degradable can be reduced by making the material more hydrophobic so that water penetration of the material will be retarded. Incorporation of saturated hydrocarbon chains onto the backbone of the polymer will result in a material that is substantially more hydrophobic. The rate of degradation can be increased by making the material more hydrophilic. Additionally, the hydrophobic or hydrophilic nature of the material can be modified by physically blending in compounds which are either hydrophobic or hydrophilic to the material without being chemically bound to any of its constituents.

A further strategy for controlling the degradation time of materials of the present invention is to vary the crystalline structure of the polymer in the materials. For polymers which are more crystalline and ordered in their molecular structure, the ability of water to infiltrate and hydrolytically degrade polymers is reduced. Thus, by producing materials which are less crystalline in structure, the rate of degradation will be increased. For example, by incorporating modifiers, such as plasticizers, into a polymer, the crystalline nature of the material will be reduced. Additionally, polymers which are homopolymers are typically more crystalline in nature than copolymers or polymer blends. Further, the crystallinity of the materials, such as films, can be increased by orientation, including uniaxial and biaxial orientation, as described more fully below.

Additionally, materials of the present invention can be coated or laminated with protective layers to exclude water to prevent hydrolytic degradation. For example, a material can be coated with some abrasion prone material which upon being discarded would likely be abraded, thus allowing moisture to infiltrate and hydrolytically degrade the polymer.

A further degradation control strategy is to control the surface area of the material. At higher surface area to volume ratios, materials of the present invention will degrade more quickly because of greater exposure to environmental moisture. Thus, materials of the present invention can be formed into various product shapes having varying degrees of surface area.

A further strategy for controlling the rate of degradation of materials of the present invention is to incorporate compounds into the material which have the capacity to absorb and isolate water from the degradable polymer. Such a compound slows the rate of degradation until its capacity for absorbing and isolating water is exceeded. In excess of that capacity, further exposure to moisture allows subsequent hydrolytic degradation of the polymeric material.

The rate of degradation of certain products can also be controlled by forming product structures which place or are capable of inducing physical stresses on the degradable polymeric material, such as a torsional stress. Such stresses increase susceptibility of the material to degradation.

Another strategy for increasing the rate of degradation of materials of the present invention is to incorporate into the polymer or otherwise incorporate into the material compounds providing the nutritional requirements for microorganisms which are capable of biodegrading degradation products of the polymer. For example, polylactic acid can be hydrolytically degraded to lactic acid, and subsequently biodegraded by a variety of microorganisms. Such microorganisms also require a source of nitrogen in addition to carbon from lactic acid for balanced growth. Thus, for example, a polylactic acid-based material can also incorporate a compound which includes nitrogen, phosphate and other salts and metals for the purpose of providing a more available nutritional source for microorganisms, thus speeding biodegradation.

While an important characteristic of the present materials is their degradability, it should be recognized that to be commercially useful, the materials need to be stable, that is, non-degradable for a period of time and under conditions such that they are commercially useful for intended product applications. Representative stability parameters are provided below for various material types.

The modifier of the present materials is a compound which introduces pliability, flexibility and toughness into a polymer composition to an extent not found in the polymer-only composition. Also, addition of modifiers to the polymer composition can reduce the melt viscosity of the polymer and lowers the temperature, pressure, and shear rate required to melt form the polymer. The modifier also can prevent heat build-up and consequent discoloration and molecular weight decrease during processing, such as extrusion forming of the polymer. Further, the modifier can add impact resistance to the polymer which is not found in the polymer-only composition. Thus, the modifier of the present materials can be considered as a compatibilizer, flexibilizer or plasticizer.

The modifier is also considered to lower the glass transition temperature ($T_g$) of a polymer. Typically, the modifier of the present materials will modify the $T_g$ of the various materials to varying degrees, depending upon the intended end use of the material. In discussion of various specific embodiments of materials of the present invention, which are discussed below, various $T_g$ parameters are provided.

A further characteristic of the present materials is that the degradable polymer and the modifier are both nontoxic. While a number of references identify the use of degradable polymers in limited areas of product applications, an important characteristic of the present invention is the recognition that degradable polymer compositions can be effectively modified with the modifier in which both the polymer and modifier are nontoxic. This recognition is significant in relation to the variety and nature of the material discussed herein which can be produced in high volume and discarded into the environment.

The reference to the polymer and modifier of the present invention being non-toxic refers to the materials being non-toxic subsequent to processing, during use and subsequent to discard into the environment, including the degradation products of the polymer being nontoxic. For example, a material such as glycerin, which is on the FDA generally regarded as safe (GRAS) list, can be used as a plasticizer, but under certain processing conditions can be converted to acrolein, which is a suspected carcinogen. Thus, the various materials of the present invention are processed so that otherwise non-toxic materials are not converted to toxic materials.

As used herein, the term "nontoxic" generally refers to substances which, upon ingestion, inhalation, or absorption through the skin by a human or animal, do not cause, either acutely or chronically, damage to living tissue, impairment of the central nervous system, severe illness or death. The term "nontoxic" can also refer to compounds, the hydrolysate or metabolites of which can be incorporated innocuously and without harm to the ecosystem. Preferably, the nontoxic polymer and modifier of the present materials are generally regarded as safe (GRAS) as that term is used by the United States FDA, or any other similar classification which may be used in the future. The toxicity level, as indicated by the Hazardous Substance Data Base of the National Library of Medicine, is an important factor in determining the suitability of each polymer and modifier for each application.

A further important characteristic of the present degradable materials is that the modifier and degradable polymer are compatible. While the concept of compatibility is discussed in more detail below, the following overview of the concept is presented before discussing specific polymer and modifier chemistry. A compatible modifier generally refers to a modifier which is intimately dispersible, as that term is defined below, in the polymer and to a polymer which is swellable in the modifier. As used herein, where the modifier is a liquid at the mixing temperature, the term "swellable" means that the polymer will expand in volume to at least about 120% of its initial volume in the presence of excess modifier.

A further aspect of the present materials is that the modifier component is nonvolatile. Thus, an important characteristic of the present materials is that during polymerization and processing of the materials, the modifier does not volatilize so that subsequent to polymerization and processing of the polymer composition into materials, the modifier substantially remains in the materials. Typically, a nonvolatile modifier refers to a modifier in a polymer/modifier material in which less than about 25 weight percent of the modifier initially present either before polymerization or before processing is lost due to volatilization of the modifier during the production of the material, more preferably less than about 2 weight percent, and even more preferably less than about 1 weight percent. Such modifiers are typically compounds which have a vapor pressure of less than about 50 Torr at 180° C. more preferably less than about 10 Torr at 180° C., and even more preferably less than about 1 Torr at 180° C. Such modifiers typically have a boiling point above about 280° C. at atmospheric pressure, more preferably above about 340° C., and even more preferably above about 400° C.

A further aspect of the nonvolatility of the modifier of the present invention is that the modifier can be nonvolatile due to strong polar characteristics of the modifier. Such polar characteristics are illustrated by those of the discussion below regarding the role of polar characteristics in compatibility of the polymer and modifier.

Portions of the prior art disclose compositions which include degradable polymers and compounds having some type of plasticizing effect for use, for example, as a processing aid. Many such compounds, however, are volatile under the processing conditions described. Thus, upon processing, such as in an extruder, processing temperatures in the extrusion process cause the compound to volatilize. Such volatilized compounds can coat the extrusion apparatus, thereby hindering effective production of material. Additionally, loss of the compound due to volatilization alters the chemical makeup of the composition.

Those skilled in the art will recognize the difference between a melt-processing aid and a modifier, such as a plasticizer. The former permits easier processing, i.e., lower processing temperatures and viscosities of the polymer melt, while the latter imparts an attenuation of certain end-use properties, e.g., modulus. In some instances, it is preferable to have a volatile additive for use as a melt processing aid so that processing is facilitated, and following processing, the additive can be removed by volatilization to allow more desirable strength or other physical property to develop. For example, lactide can be added as a processing aid to polylactide in a twin-screw compounder that transports the melt blend to an extruder where the lactide is removed, either at a later zone or the die of the extruder. In this way, stiff polylactide compositions without a modifier can be melt fabricated without sacrificing processability.

A further aspect of the materials of the present invention is that the modifier is nonfugitive. The term nonfugitive refers to an modifier that does not escape from the material during the useful life of the materials. That is, the modifier remains substantially intimately dispersed in the polymer for the useful life of the material. For example, fugitive materials, which may initially be present as a discrete phase, can become soluble in the polymer and migrate towards the surface of a material to form a surface film or vapor. That is, fugitive modifiers are not compatible with the polymer over time to an extent which impedes the intended function of the material. Typically, modifiers in a polymer/modifier material are considered nonfugitive when less than about 30 weight percent of the modifier present in the processed material is lost due to becoming fugitive during the useful life of the material, that is, during the time period from after the material is processed until the time the ultimate consumer discards the materials, more preferably less than about 10 weight percent and more preferably less than about 1 weight percent.

The polymer of the present composition can be selected from a variety of nontoxic degradable polymers. Typically, the polymer should have a weight average molecular weight of between about 5,000 and about 1,500,000. Appropriate molecular weights will vary according to desired material type and will be discussed more fully below. Appropriate molecular weights of polymers in accordance with parameters discussed herein can be achieved by those skilled in the art by known methods.

The polymer of the present composition can be a homopolymer, a copolymer, or a physical blend of homopolymers and/or copolymers. Typically, the polymer of the present materials includes repeating monomer or comonomer units which are selected from the following group and which polymers are non-toxic and degradable:

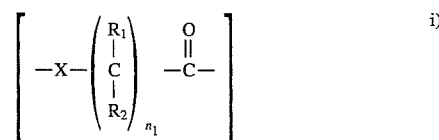   i)

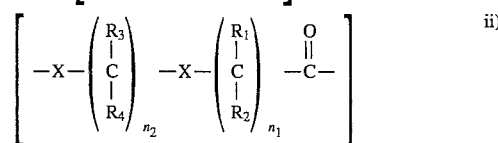   ii)

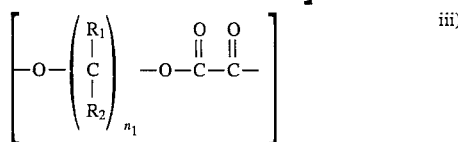   iii)

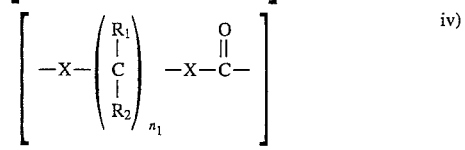   iv)

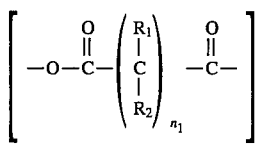

wherein X is the same or different and is O or NR' with R' independently being H, hydrocarbyl, or substituted hydrocarbyl; $R_1$, $R_2$, $R_3$ and $R_4$ can be the same or different and are hydrogen, hydrocarbyl containing 1 to 24 carbon atoms, or substituted hydrocarbyl containing 1 to 24 carbon atoms, and where $n_1$ and $n_2$ can be the same or different and are an integer of from 1–12.

The polymer of the present invention typically includes the above repeating monomer or comonomer units in an amount of at least about 5 weight percent, more preferably at least about 10 weight percent and more preferably at least about 20 weight percent. Preferably, the polymer includes a high enough percentage of polymerized monomers which are hydrolytically degradable so that, upon degradation, polymer fragments of less than about 600 molecular weight are produced because such polymer fragments are small enough to be metabolized by microorganisms.

The nontoxic degradable polymer of the present materials can be more particularly characterized as having repeating monomer or comonomer units selected from the group consisting of:

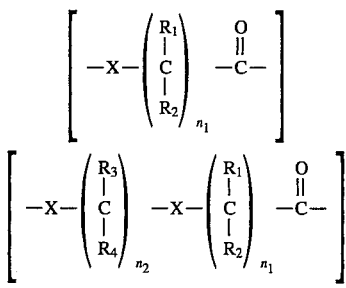

wherein X is the same or different and is O or NR' with R' independently being H, hydrocarbyl, or substituted hydrocarbyl; $R_1$ and $R_2$ can be the same or different and are hydrogen, hydrocarbyl containing 1 to 24 carbon atoms, or substituted hydrocarbyl containing 1 to 24 carbon atoms, and where $n_1$ and $n_2$ can be the same or different and are an integer of from 1–12.

The polymer of the present materials is more particularly characterized as comprising repeating monomer or comonomer units derived from monomers selected from the group consisting of alpha-hydroxycarboxylic acids, betahydroxycarboxylic acids, gamma-hydroxycarboxylic acids, delta-hydroxycarboxylic acids, epsilon-hydroxycarboxylic acids, beta-lactones, gamma-lactones, delta-lactones, epsilon-lactones, beta-lactams, gamma-lactams, delta-lactams, epsilon-lactams, cyclic diesters of alphahydroxycarboxylic acids, dioxanones, substituted variations of the foregoing compounds, and combinations thereof. The polymer of the present materials is further characterized as comprising repeating monomer or comonomer units derived from monomers selected from the group consisting of lactic acid, glycolic acid, epsilon-hydroxycaproic acid, lactide, glycolide, epsilon-caprolactone, delta-valerolactone, substituted variations of the foregoing compounds, and combinations thereof.

In a more preferred embodiment, the polymer comprises repeating monomer or comonomer units derived from lactic acid which can be the result of direct polymerization of lactic acid or the polymerization of lactide. Preferably, the polymer typically includes more than about 50 weight percent repeating units derived from lactic acid or lactide, and more preferably greater than about 75 weight percent. In another embodiment, the polymer is prepared from polymerization of a composition including lactide in which greater than about 50% by weight of the lactide is optically active and less than 50% is optically inactive lactide selected from the group consisting of racemic D,L-lactide and meso D,L-lactide.

In a more preferred embodiment of the invention the polymer is polylactic acid and has the repeating units of the formula,

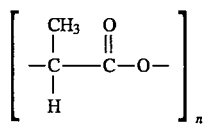

wherein n is the number of repeating units and n is an integer equal to at least about 150 and preferably $150 \leq n \leq 20{,}000$. Preferably the unoriented composition has the physical properties of: a tensile strength of about 300 to about 20,000 psi, an elongation to failure of about 2 to about 1,000 percent, and a tangent modulus of about 1,000 to about 500,000 psi.

Those skilled in the art will recognize that this wide latitude of properties must be accommodated to serve the varied needs of the plastics industry. A review of this range of properties is found in copending, commonly assigned U.S. patent application Ser. No. 07/579,005, "Biodegradable Packaging Thermoplastics From Polylactic Acid". For example, presently used commodity thermoplastics vary considerably by use. Stiff thermoforms, such as are used in salad covers are typically served by thermoplastics such as polystyrene, which will be oriented to have a tensile strength of about 7500 psi, and elongation to break of about 4%, and an elastic modulus of about 350,000 psi. At the other extreme, pliable films for trash bags use plastics with a tensile strength of about 1500 psi, elongations of 500%, and moduli of about 25,000 psi.

The polymer of the present materials can be further characterized as one which does not bioaccumulate. As used herein, the term "bioaccumulation" refers to an increase in concentration of a substance over time in a human or animal upon repeated ingestion, inhalation or absorption through the skin by a human or animal, or alternatively, one which does not accumulate in soil or waterways to a level which is toxic to plants or animals.

The polymer of the present materials is typically present in the materials in amounts between about 99 weight percent and about 50 weight percent, more preferably between about 98 weight percent and about 65 weight percent, and even more preferably between about 95 weight percent and about 80 weight percent.

The polymer of the present materials can be prepared by a variety of polymerization techniques. Preferably, the polymerization reaction is conducted in the liquid phase in a closed, evacuated vessel. Alternatively, the polymer can be prepared at atmospheric pressure with the polymerization mixture blanketed by an inert gas such as, for example, nitrogen. If the polymerization reaction is conducted in the presence of oxygen or air, some discoloration can occur with a resulting decrease in molecular weight and tensile strength.

Typically, the polymerization is conducted above the melting point of the monomers or comonomers and below a temperature at which degradation of the resulting polymer occurs. For example, in the case of production of polylactic acid from the polymerization of L-lactide and/or D,L-lactide, the polymerization can be conducted at a temperature of between about 95° C. and about 200° C., more preferably between about 110° C. and about 190° C., and more preferably between about 160° C. and about 175° C.

In a preferred embodiment of the polymerization reaction, polymerization is conducted at temperatures where the polymerization is sluggish in its later stages so as to trap residual monomer in the viscous polymer melt to function as an modifier for the polymer. Without intending to be bound by theory, it is believed that by conducting the polymerization reaction under such conditions, the reactant monomer mixture melts to a mobile fluid that is an intimate mixture of the monomers or comonomers. Further, the fluid melt is polymerized by catalyst present to form an increasingly viscous solution and eventually unreacted monomer is trapped in association with the polymer as an intimate dispersion. The monomer can no longer readily react since the reaction is extremely diffusion controlled and cannot efficiently contact the low concentration of active end-groups of the polymer. Further, the polymerization ceases or slows considerably so that, at room temperature, the blend of monomer and polymer are an intimate dispersion that can impart pliability, clarity, and flexibility to the composition. If residual catalyst is deactivated by contact with ambient moisture, then subsequent melt-fabrication or other thermal processing treatment does not initiate further polymerization. The resulting composition remains intimately dispersed. For example, in the case of the production of poly(lactic acid) in which it is desired to retain residual monomer as a plasticizer from a mixture of L-lactide and D,L-lactide, the temperature of polymerization in this embodiment should be maintained low but above the melting points of the two monomers, or above 127° C.

The catalysts used in the polymerization reaction of the present invention can be tin salts and esters of carboxylic acids containing up to 18 carbon atoms. Examples of such acids are formic, acetic, propionic, lactic, butyric, valeric, caproic, 2-ethylhexanoic, caprylic, pelargonic, capric, lauric, myristic, palmitic, stearic, and benzylic acids. For example, good results can be obtained in the case of production of polylactic acid with the use of stannous acetate and stannous caprylate.

The catalyst is used in normal catalytic amounts for polymerization. For example, a stannous 2-ethylhexanoate catalyst concentration in a range of about 0.001 to about 2 percent by weight, based on total weight of the monomers or comonomers, is suitable. A catalyst concentration in the range of about 0.01 to about 1.0 percent by weight is preferred. Particularly preferred is a catalyst concentration in the range of about 0.02 to about 0.5 percent by weight. The exact amount of catalyst in any particular case depends to a large extent upon the catalyst employed and the operating variables, including time, temperature and the desired rate of reaction.

The reaction time of the polymerization process is dependent on other reaction variables, including reaction temperature, polymerization catalyst, amount of catalyst, degree of mixing, and whether a solvent is used. The reaction time can vary from a matter of minutes to a period of hours or days, depending upon the particular set of conditions which is employed. Heating of the mixtures of monomers or comonomers is continued until the desired level of polymerization is attained. For example, the extent of polymerization can be determined by analysis for residual monomers. For example, as discussed above, the reaction temperature can be chosen so that polymerization is stopped prior to complete reaction of all monomers or comonomers to provide for a polymer composition having residual monomer and comonomer. The reaction can be halted at such time that the polymer composition has the desired degree of conversion to attain the desired level of residual monomer and comonomer. In a preferred embodiment of the present invention, approximately 2–30% by weight of monomer or comonomer is left unreacted.

In general, it is preferred to conduct the polymerization in the absence of impurities which contain active hydrogen since the presence of such impurities tends to deactivate the catalyst and/or increase the reaction time. It is also preferred to conduct the polymerization under substantially anhydrous conditions.

The polymer of the present invention can be prepared by bulk polymerization, suspension polymerization or solution polymerization. The polymerization can be carried out in the presence of an inert normally-liquid organic vehicle such as, for example, aromatic hydrocarbons, e.g., benzene, toluene, xylene, ethylbenzene and the like; oxygenated organic compounds such as anisole, dimethyl and diethyl esters of ethylene glycol; normally-liquid saturated hydrocarbons including open chain, cyclic and alkyl-substituted cyclic saturated hydrocarbons such as hexane, heptane, cyclohexane, decahydronaphthalene and the like.

The polymerization process can be conducted in a batch, semi-continuous, or continuous manner. In preparing the monomeric reactants and catalysts for subsequent polymerization, they can be admixed in any order according to known polymerization techniques. Thus, the catalyst can be added to one comonomeric reactant. Thereafter, the catalyst-containing comonomer can be admixed with another comonomer. In the alternative, comonomeric reactants can be admixed with each other. The catalyst can then be added to the reactant mixture. If desired, the catalyst can be dissolved or suspended in an inert normally-liquid organic vehicle. If desired, the monomeric reactants either as a solution or a suspension in an inert organic vehicle can be added to the catalyst, catalyst solution or catalyst suspension. Still further, the catalyst and comonomeric reactants can be added to a reaction vessel simultaneously. The reaction vessel can be equipped with a conventional heat exchanger and/or mixing device. The reaction vessel can be any equipment normally employed in the art of making polymers. One suitable vessel, for example, is a stainless steel vessel. The plasticizer to be used or a solvent can be blended into the polymer to aid in removal of the polymer material from the reactor vessel.

The modifier of the present materials, as discussed above, is compatible with the polymer, is nonvolatile and is nonfugitive. The modifier is preferably selected from the group consisting of dicarboxylic acids, derivatives of dicarboxylic acids, polyesters of dicarboxylic acids, tricarboxylic acids, derivatives of tricarboxylic acids, polyesters of tricarboxylic acids, cyclic diesters of alpha-hydroxycarboxylic acids, derivatives of cyclic diesters of alpha-hydroxycarboxylic acids, oligomers of cyclic diesters of alpha-hydroxycarboxylic acids, beta-lactones, delta-lactones, gamma-lactones, ε-lactones, oligomers of alpha-hydroxycarboxylic acids, esters of oligomers of alpha-hydroxycarboxylic acids, benzoic acid derivatives, epoxy derivatives, glycol derivatives, phthalic acid derivatives, phosphoric acid derivatives, ketones, amides, nitriles, and combinations of the foregoing.

The modifier is more preferably selected from the group consisting of adipic acid derivatives, azelaic acid derivatives, cyclic esters of oligomers of lactic acid, esters of oligomers of lactic acid, citric acid derivatives, polyesters of adipic acid, polyesters of azelaic acid, polyesters of sebacic acid, sebacic acid derivatives, benzoic acid derivatives, epoxy derivatives, glycol derivatives, phthalic acid derivatives, phosphoric acid derivatives, and combinations thereof.

The modifier is more preferably selected from the group consisting of di-n-hexyl adipate, bis(2-ethylhexyl)adipate, diisodecyl adipate, bis(2-butoxyethyl) adipate, bis(2-ethylhexyl)azelate, lactide, epsilon-caprolactone, glycolide, delta-valerolactone, oligomeric lactic acid, oligomeric lactic acid ethyl ester, acetylated lactoyllactate ethyl ester, tri-n-butyl citrate, tri-n-butyl acetylcitrate, diethylene glycol dibenzoate, dipropylene glycol dibenzoate, epoxidized soy oil, 2-ethylhexyl epoxy tallate, diethylene glycol dinonanoate, triethylene glycol di(2-ethylbutyrate), pentaerythritol esters, alkoxy sucrose and glucose, acylated sucrose and glucose, alkylated and acylated glycols, starch esters, N-acylated amino acid esters, amide derivatives and oligomers of N-acylated amino acid esters, polyethylene glycol esters, tri(2-ethylhexyl)phosphate, diemethyl phthalate, diethyl phthalate, butyl 2-ethylhexyl phthalate, bis(2-ethylhexyl)phthalate, dicyclohexyl phthalate, diphenyl phthalate, adipic acid polyester with molecular weight from about 190 to about 6000, azelaic acid polyester with molecular weight from about 232 to about 7500, sebacic acid polyester with molecular weight from about 246 to about 8000, di-n-butyl sebacate, and bis(2-ethylhexyl)sebacate, and combinations thereof.

The modifier is more preferably selected from the group consisting of di-n-hexyl adipate, bis(2-butoxyethyl)adipate, bis(2-ethylhexyl)azelate, lactide, epsilon-caprolactone, glycolide, delta-valerolactone, oligomeric lactic acid, oligomeric lactic acid ethyl ester, tri-n-butyl citrate, tri-n-butyl acetylcitrate, dipropylene glycol dibenzoate, epoxidized soy oil, 2-ethylhexyl epoxy tallate, diethylene glycol dinonanoate, triethylene glycol di(2-ethylbutyrate), butyl 2-ethylhexyl phthalate, bis(2-ethylhexyl)phthalate, dicyclohexyl phthalate, adipic acid polyester with molecular weight from about 190 to about 6000, azelaic acid polyester with molecular weight from about 232 to about 7500, sebacic acid polyester with molecular weight from about 246 to about 8000, di-n-butyl sebacate, and combinations thereof.

The modifier is more preferably selected from the group consisting of dicarboxylic acids, derivatives of dicarboxylic acids, polyesters of dicarboxylic acids, tricarboxylic acids, derivatives of tricarboxylic acids, polyesters of tricarboxylic acids, cyclic diesters of alpha-hydroxycarboxylic acids, derivatives of cyclic diesters of alpha-hydroxycarboxylic acids, oligomers of cyclic diesters of alpha-hydroxycarboxylic acids, betalactones, delta-lactones, gamma-lactones, ε-lactones, oligomers of alpha-hydroxycarboxylic acids, esters of oligomers of alpha-hydroxycarboxylic acids, and combinations of the foregoing.

The modifier is further preferably selected from the group consisting of adipic acid derivatives, azelaic acid derivatives, cyclic esters, oligomers of lactic acid, esters of oligomers of lactic acid, citric acid derivatives, polyesters of adipic acid, polyesters of azelaic acid, polyesters of sebacic acid, sebacic acid derivatives, and combinations thereof.

The modifier is further preferably selected from the group consisting of di-n-hexyl adipate, lactide, epsilon-caprolactone, glycolide, delta-valerolactone, oligomeric lactic acid, oligomeric lactic acid ethyl ester, tri-n-butyl acetylcitrate, adipic acid polyester with molecular weight from about 190 to about 6000, azelaic acid polyester with molecular weight from about 232 to about 7500, and combinations thereof.

In a preferred embodiment of the present invention, and particularly when the polymer includes lactic acid-derived repeating units, preferred modifiers include lactic acid, lactide, oligomers of lactic acid, oligomers of lactide and mixtures thereof. The preferred oligomers of lactic acid and oligomers of lactide are defined by the formula:

$$HO(-\underset{H}{\overset{CH_3}{\underset{|}{C}}}-\overset{O}{\overset{\|}{C}}-O-)_mH$$

where m is an integer: $2 \leq m \leq 75$. Preferably m is an integer: $2 \leq m \leq 10$.

Further modifiers useful in the invention include oligomeric derivatives of lactic acid and lactide selected from the group defined by the formula:

$$R'O(-\underset{H}{\overset{CH_3}{\underset{|}{C}}}-\overset{O}{\overset{\|}{C}}-O-)_qR$$

where R=H, alkyl, aryl, alkylaryl or acetyl, and R is saturated, where R'=H, alkyl, aryl, alkylaryl or acyl, and R' is saturated, where R and R' cannot both be H, where q is an integer: $2 \leq q \leq 75$. Preferably, q is an integer: $2 \leq q \leq 10$.

As discussed above, the modifier of the present invention is nontoxic. Preferred nontoxic modifiers of the present invention include modifiers selected from the group consisting of acetyl tributyl citrate, lactide, glycolide, lactic acid esters, dimethyl adipate, diethyl adipate, caprolactone, acetyl triethyl citrate, bis 2-ethyl hexyl sebacate, bis 2-ethyl hexyl adipate, dibutyl sebacate, and triethyl citrate. Even more preferred nontoxic modifiers of the present invention are selected from the group consisting of acetyl tributyl citrate, lactide, glycolide, lactic acid esters, dimethyl adipate, diethyl adipate, caprolactone, acetyl triethyl citrate, bis 2-ethyl hexyl sebacate and bis 2-hexyl adipate.

The modifier of the present invention, in one embodiment, is characterized by being hydrolytically degradable, as that term is described above with regard to the polymers of the various materials. The modifier, in a further embodiment, is considered to be biodegradable, as that term is described above with regard to the polymer of the various materials. The modifier is also characterized in a further embodiment as being a compound that is environmentally benign and does not bioaccumulate, as that term is used above with regard to the polymer of the various materials.

The modifier in the present materials is preferably in an amount between about 1 weight percent and about 60 weight percent, more preferably between about 5 weight percent and about 50 weight percent, and more preferably between about 10 weight percent and about 40 weight percent.

An important aspect of the present materials is the use of a modifier which is compatible with the polymer of the present materials. The term "compatibility" refers to the relationship between the polymer and the modifier. More particularly, the term "compatibility" refers to a modifier which is thermally compatible with the polymer composition such that upon processing and use of the composition, the modifier and polymer remain as uniform mixtures, i.e., one that is not cheesy in appearance and without significant change in the relative proportions of the components. Compatible mixtures typically are clear, non-oily, swelled and the material does not stress craze easily. One useful indicator of the compatibility of a modifier and polymer is the difference between the solubility parameters of the polymer and modifier. The term "solubility parameter" is also referred to as Hildebrand constant and is given in units of energy per volume, such as calories per cubic centimeter (cal/cm$^3$). Solubility parameters can be calculated by known methods shown in the literature. A solubility parameter is a measure of the internal attractive force that molecules of the same compound have for each other. Thus, for two different compounds having similar solubility parameters, the two compounds are likely to be readily as soluble with molecules of the other compound as they are with molecules of the same compound. It should be noted that while solubility parameters are useful in assessing compatibility, they are not absolute predictors. Calculations of solubility parameters, for instance, do not account for all aspects of the chemical structure of a molecule. Thus, chemical features, such as polar character which is discussed below, and others, can make otherwise incompatible species compatible and vice versa.

Typically, the solubility parameters of the polymer and modifier are within about 1.0 cal/cm$^3$, preferably within about 0.75 cal/cm$^3$, and more preferably within about 0.5 cal/cm$^3$. The solubility parameters of the modifier and the polymer are also typically each in the range of from about 7.5 cal/cm$^3$ to about 16.5 cal/cm$^3$, more preferably between about 8.0 cal/cm$^3$ to about 12.0 cal/cm$^3$ and more preferably between about 9.0 cal/cm$^3$ and about 11.0 cal/cm$^3$.

A first parameter for determining compatibility is the difference in solubility parameters between the polymer and the modifier. It has been surprisingly found, however, that polymer/modifier combinations which have solubility parameter differences outside of the parameters discussed above, can be compatible if the polymer and modifiers have suitable polar characteristics which provide sufficient polar attraction between the species to make the polymer and modifier compatible. For example, it has been found that a polymer and modifier having solubility parameters of about 9.57 and about 14.39, respectively, are compatible. In this instance, the polymer is a 90/10 L-lactide/D,L-lactide copolymer and the modifier is N-ethyl o,p-toluene sulfonamide. Relevant polar characteristics, include hydrogen bonding index, dielectric constant, and dipole moment.

One measure of polar interaction between two materials is the hydrogen bonding index. This index is derived from the infrared spectral shifts of deuterated methanol when complexed with the substance under investigation. Preferably, the hydrogen bonding indices of the polymer and modifier are within less than about 10 units of each other, more preferably, less than about 5 units of each other and more preferably less than about 2 units of each other.

The dielectric constant of a substance refers to its ability to resist the transmission of an electrostatic force from one charged body to another. Preferably, the dielectric constants of the modifier and polymer, at 25° C., are within about 20 units of each other, more preferably within about 5 units of each other, and even more preferably within about 2 units of each other.

A further component of compatibility between the polymer and modifier is the relative dipole moments of the polymer and modifier. The term "dipole moment" refers generally to the polarity of molecules and, more particularly, is the distance between charges multiplied by the quantity of charge in the electrostatic portions of the molecule. Typically, the dipole moments of the polymer and modifier are within about 6 units of each other, more preferably within about 2 units of each other, and even more preferably within about 1 unit of each other.

Another aspect of compatibility is the similarity between the polymer and modifier in terms of hydrophilic lipophilic balance ("HLB"). HLB is a measure of a material's relative hydrophilic and lipophilic nature. HLB has scale of zero to 20 in which a fully hydrophilic material would be 20 and a saturated hydrocarbon would be zero. The HLB of compounds with both hydrophilic and lipophilic portions is determined by dividing the weight percent of the hydrophilic portion by 5.

The HLB value of polylactic acid is approximately 10 and that of polyglycolic acid is approximately 15. Lactide has an HLB of 12 and glycolide is 15. A typical good plasticizer for polylactic acid is dimethyl adipate (HLB= 10). This plasticizer did not function with polyglycolic acid. A plasticizer that functioned marginally with polylactic acid was lauronitrile. It has an HLB of 3, but its hydrophilic group is extremely polar.

The HLB values of the plasticizer should be within about 4 units, and preferably within 2 units, of the polymer to be plasticized. Special circumstances can stretch the range to about 7 HLB units.

It has also been found that when polymers of the present invention are able to adopt varied three-dimensional configurations, the polymers are compatible with a wide variety of modifiers. For example, polymers which are less crystalline in nature are typically able to adopt more varied three-dimensional structures than polymers which are relatively crystalline. Copolymers are usually less crystalline in nature than homopolymers. As a specific example, a copolymer with monomeric units selected from L-lactide, D-lactide and glycolide is typically less crystalline than homopolymers of-any of the three materials.

Typically, polymers which have less than about 20 percent crystallinity, more preferably less than about 10 percent crystallinity, and more preferably less than about 5 percent crystallinity have suitably varied three-dimensional configurations for advantageous compatibility characteristics. Crystallinity can be measured by various standard techniques. In addition, as noted above, the polymers of the present invention are preferably copolymers, more preferably copolymers in which no one monomer constitutes more than about 95 weight percent of the polymer, more preferably no one monomer constitutes more than about 85 weight percent of the polymer and more preferably no one monomer constitutes more than about 75 weight of the polymer.

A further aspect of the modifier of the present materials is that it is preferably thermally stable. As used herein, the term "thermal stability" refers to a compound having a stable chemical structure and/or which does not become discolored at a given temperature. Preferred modifiers of the present materials are typically thermally stable at temperatures up to about 130° C., more preferably up to about 175° C., and even more preferably up to about 200° C. The modifier of the present materials also preferably does not have an odor.

A further characteristic of the present materials is that the modifier is intimately dispersed throughout the polymer. The term "intimate dispersion" refers to a material which is macroscopically homogenous in appearance and which has microscopic domain sizes of modifier and polymer which are typically smaller than about 10 microns and more preferably smaller than about 1 micron. Intimate dispersion of a modifier in a polymer can be achieved by various methods. For example, in the instance when the modifier of the present invention is also a monomer or comonomer used in preparation of the polymer, intimate dispersion of the modifier can be achieved by prematurely terminating polymerization of the monomers or comonomers so that some residual portion of the monomers remain in the composition as modifiers. Intimate dispersion of modifiers and polymers can also be achieved by physical blending and aggressive mixing of a modifier and polymer or, for example, by dissolving the polymer and modifier in a common solvent which is then removed by evaporation or some other means.

The materials of the present invention include a polymer and modifier as generally discussed above. After formulation of the various blends, the polymer/modifier composition typically has suitable physical characteristics so that the composition can be readily processed into various materials under temperatures which do not significantly degrade the polymer or cause the modifier to volatilize. In particular, the polymer formulation has a low enough viscosity for suitable processing.

The compositions used for the materials of the present invention can include various other components, such as crosslinking agents, pigments, fillers, antioxidants, UV light absorbers, fungicides and other additives known to those skilled in the art.

As discussed above, the present invention is directed to various materials which include the polymer and modifier of the present invention. The various materials of the present invention have varying chemical and physical characteristics which are relevant to their intended uses. The materials of the present invention include the following types: films, molded products, laminates, foams, nonwovens, adhesives and coatings.

Film material of the present invention is made from compositions as described above. The term film, as used herein, refers to a material type which is a film in its final product configuration and does not refer to intermediate source materials which are subsequently processed into non-film products. The term films includes material commonly identified as a film with thicknesses of less than about 20 mil and also is intended to include materials which may also be termed sheets, including materials with thicknesses up to about 50 mil. Such films can be prepared to simulate the properties of common materials, such as polyethylenes, polystyrenes, and vinyls. The desired molecular weight distribution for each application is achieved by adjustment of the polymerization conditions and by post-polymerization processing. Choices and percentages of modifier(s) affect flexibility and processing temperatures as well as the degradation rate. Such films can be produced by a variety of known processes. For example, films can be prepared by compression molding processes. Suitable films can also be prepared by extrusion processes, including blown film processes, melt-extruded casting, and by casting solutions of the polymer composition and then recovering the solvent.

Thermal annealing and quenching are two methods that control the morphology of the film to emphasize selected properties. Quenching as used herein indicates that the temperature of a material is dropped rapidly to prevent extensive crystallization of the polymer. Crystallization of polymers is a slow process, requiring minutes to hours to fully accomplish. When crystallization is desired, the temperature is held above the glass-transition temperature, $T_g$, for some time to allow the molecules to order themselves into extensive crystalline lattices. This process is called annealing. When cooled rapidly from an amorphous melt, the polymer does not have the time required for crystallization and remains largely amorphous. The time required to quench depends on the thickness of the sample, its molecular weight, melt viscosity, compositions, and its $T_g$. Note that melt viscosity and $T_g$ are lowered by plasticization, which also impedes alignment of the polymer molecules, i.e., plasticization facilitates quenching. Thin films obviously cool very quickly because of their high surface-to-volume ratio while thicker films cool more slowly with their greater thicknesses. Regular structures such as homopolymers order more easily and crystallize more quickly than more random structures such as a copolymer.

Quenching to an amorphous state requires that the polymer or copolymer in an amorphous melt is rapidly cooled from its molten state to a temperature below its $T_g$. Failure to cool rapidly allows spherulitic crystallinity to develop, that is, crystalline domains of submicron to micron size. The latter scatters light and the polymer specimens become opaque. These crystalline forms have improved stability to heat distortion. This spherulitic crystallinity is often called short range order-long range disorder since the crystallites are separated by amorphous regions. However, the crystallites act as pseudo crosslinks to maintain dimensional stability above the $T_g$ but below their melting points. Alternatively stability to heat distortion can be obtained by orienting an amorphous polymer above its $T_g$ but below its melting point. Here, the polymer molecules are stretched to allow some long range ordering, then "heat set" to permit the ordering to complete, that is, given some time to anneal. The amorphous polymer is thereby crystallized into a different order, called long-range order, short range disorder. Transparency and resistance to heat distortion are favored.

Films of the present invention can be oriented or not and can be shrinkable or not. Orientation refers to stretching a film in one direction which allows for alignment and ordering of the polymer molecules along the direction of stretching. The stretching can be 2 or more times the original length of film in the direction of stretching. Orienting can be uniaxial, which is typically in the direction the film travels as it is processed. Alternately, orienting can be biaxial which is typically in the direction the film travels as it is processed and in a second direction transverse to the first. Orientation is conducted at a film temperature above the $T_g$ of the film and below its melting point. Biaxially oriented films are useful as shrinkable films in shrink wrap packaging.

Biaxially oriented films can be made not shrinkable by heat setting the films. To heat set oriented films, films are restrained at the dimensions they are stretched to after heating to a temperature above the $T_g$ and below the melting point. This procedure allows internal tension in the film to relax and upon cooling the film is non-shrinkable.

As noted above, films of the present invention can be prepared having a variety of product characteristics. Such films can have polystyrene-like properties, low density polyethylene-like properties, high density polyethylene-like properties, polypropylene-like properties and polyvinyl chloride-like properties. Polystyrene-like films of the present invention typically are transparent, and semicrystalline, and have a weight average molecular weight between about 50,000 and 500,000; are form-stable to temperatures greater than about 100° C.; have a tensile strength of between about 6,000 psi and about 8,000 psi; Shore D hardner of between about 80 and about 90; elongations to break of about 2% to about 4%; elastic moduli of greater than about 250,000 psi; and degrade under ambient conditions in about 6 to about 24 months. Low density polyethylene-like film materials of the present invention typically are sometimes transparent, not crystalline, and have a weight average molecular weight from about 50,000 to about 500,000; a $T_g$ of about room temperature, or below; tensile strengths of between about 1,500 psi and about 3,000 psi; Shore D hardner of about 50; an elongation to break to about 150% to about 1,200%; elastic moduli of between about 10,000 psi and about 50,000 psi; are not spherulitically crystalline; and are degradable under ambient conditions in about 3 to about 12 months. High density polyethylene-like materials of the present invention typically are sometimes transparent, crystalline and have weight average molecular weights of between about 50,000 and about 500,000; form-stability temperatures of about room temperature to about 80° C.; tensile strengths of between about 2,500 psi to about 4,000 psi; Shore D hardner of between about 50 and about 60; an elongation to break of between about 50% and about 500%; an elastic modulus of between about 50,000 psi and about 125,000 psi; and are degradable under ambient conditions in from about 6 to about 24 months. Polypropylene-like films of the present invention typically are sometimes transparent, usually crystalline and have a weight average molecular weight of between about 50,000 and about 500,000; a form-stability temperature of about room temperature to about 120° C.; a tensile strength of between about 4,000 and about 6,000; a Shore D hardness of about 70; an elongation to break of between about 100% and about 600%; has an elastic modulus of between about 125,000 psi and about 200,000 psi; and are degradable under ambient conditions in from about 6 months to about 24 months. Polyvinyl chloride-like films of the present invention typically are sometimes transparent, not crystalline, and have a wide range of properties with weight average molecular weights of between about 50,000 and about 500,000; $T_g$'s of below room temperature to about 100° C.; tensile strengths of between about 300 psi and about 5,000 psi; Shore D hardnesses of between about 10 and about 90; elongations to break of between about 5% and about 500%; elastic moduli of between about 500 psi and about 250,000 psi; and are degradable under ambient conditions in from about 6 months to about 24 months.

Film materials of the present invention can be made into a wide variety of product types. For example, a particularly advantageous film material of the present invention is in the form of a packaging material. Further, film materials of the present invention can be produced in other product types, such as garbage bags.

Another type of material of the present invention includes various molded products. Molded products can be made by a variety of processes, including blow molding, injection molding and thermoforming. Blow molding is employed to make hollow shapes, especially packaging containers. In the extrusion embodiment of this process, a parison is made first and then expanded to the walls of the mold cavity. The degradable polymer composition is tailored to meet extrusion blow molding processing requirements by adjustment of comonomer ratio, molecular weight of the polymer product, and choice/percentage of modifier. These processing requirements are reconciled with the end use requirements with regard to shelf life, strength, speed of onset of degradation, and other parameters. Weight-average molecular weights of over 50,000 and as high as 500,000 are desirable for these applications. There are trade-offs in molecular weight and percent modifier such that flexible bottles can be made by use of polymeric plasticizers with moderate molecular weight degradable polymers. Polymeric modifiers are not extracted into the liquid contents of containers, and the flexibility of the package renders it more impact-resistant.

Injection molding of thermoplastics is accomplished by melting the thermoplastic composition and transferring it into a mold cavity where it solidifies to conform to the shape of the mold. Injection molded products require little or no mechanical work before they are fabricated with other parts into an end use product. Injection molded products of the present invention one typically sometimes transparent and have a weight average molecular weight of between about 50,000 and about 120,000; a heat-deflection temperature of greater than about 70° C.; a tensile strength of greater than about 3,000 psi; a Shore D hardness of between about 50 and about 90; an elongation to break of between about 2% and about 25%; is an elastic modulus of between about 100,000 psi and about 400,000 psi; and are degradable under ambient conditions in from about 6 months to about 24 months.

The materials of this invention are highly suitable for injection molding because their melting points and morphology can be tailored in many different ways. The melt rheology of the materials can be adjusted to tailor the melt viscosity, shear dependence, heat-deflection temperatures, crystallization temperature, and other processing requirements. The molecular weights and distribution of molecular weight are commonly adjusted to accommodate flow- and cycle-time requirements. Because the economics of injection molding usually necessitates short cycle times, relatively low, weight-average molecular weights (less than 120,000) are desirable.

Injection molded products of the present invention typically have a weight average molecular weight of between about 50,000 and about 120,000; a heat-deflection temperature of greater than about 70° C.; a tensile strength of greater than about 3,000 psi; a Shore D hardness of between about 50 and about 90; an elongation to break of between bout 2% and bout 25%; are sometimes transparent; an elastic modulus of between about 100,000 psi and about 4000,000 psi; can be semicrystalline; and are degradable under ambient conditions in from about 6 months to about 24 months.

Thermoforming is a branch of molding that uses films or sheets of thermoplastic. Because the materials of this invention are especially easy to convert to film or sheet form that have excellent transparency, they are excellent candidates for thermoforming. The sheet must be heated to the temperature that at which it is quite flexible and then subjected to vacuum or pressure that presses the sheet against a mold, forming the desired shape. The plastic memory of these polymer-plasticizer combinations is a useful attribute in drape forming embodiments of thermoforming.

Molded products can include a number of different product types and, for example, can include products such as disposable spoons, forks and knives, bottle-like packaging containers, and various thermoforms.

Other material types of the present invention include laminates and coextrudates. Film laminates and coextruded films are composite materials in which each layer provides functional utility that complements the rest of the structure. The polymer/modifier materials of this invention provide degradability, in addition to such functions as strength, printability, and high transparency. The other layers in the laminate or coextruded structure can provide temporary protection against moisture or abrasion so that the onset of degradation is delayed until after the shelf-life and consumer-use phases have passed. The other layers may also provide essential electrical or other functions that require the layer to be nondegradable; however, the adverse environmental impact can be reduced by using the polymers of this invention for most of the weight of the product.

Laminating resins are another material of the present invention and are used as a tie-layer between dissimilar surface layers. For example, many packaging materials can be prepared using a laminating layer between so-called clayboard, boxboard, or cardboard and outer layers of thermoplastic films. Such laminated materials, for example, have layers which perform various functions, such as structural stability, gas permeability, decoration and moisture exclusion. The polymer compositions of the present invention, can be used, for example, as a transparent outer protective coating for such a laminated product, and/or provide the laminating, or tie-layer.

A laminating resin or coextrudate of the present invention typically is not crystalline and has a weight average molecular weight of between about 500 and 5,000; a $T_g$ below about room temperature; a Shore D hardness of about 0.5; an elongation to break of greater than about 300%; an elastic modulus of less than about 1,000 psi; and is degradable under ambient conditions in from about 1 month to about 3 months.

A further material type of the present invention includes foams. Foamed thermoplastics have large markets in food packaging. The materials of this invention are outstanding candidates for use in these applications because they can be melted to a high-viscosity material that can be blended with such gases as carbon dioxide or nitrogen for foam extrusion. The viscosity of the melt can be optimized by control of molecular weight, molecular weight distribution, and by modifier content. Typically, the polymer will have a molecular weight of more than 300,000 for foam extrusion. Amount and type of polymeric modifiers are especially desirable for this foam application because an elastic bubble is desirable. The solubility (under pressure) of carbon dioxide in the polymers of this invention can be exploited to control pore size of bubbles that are produced after cooling.

Foam materials of the present invention typically are semicrystalline and are not transparent, have a weight average molecular weight of between about 50,000 and about 500,000; a $T_g$ of between about 100° C. and 105° C.; and are degradable under ambient conditions in between about 6 months to about 24 months.

A further material of the present invention includes spun-bonded nonwoven material. The term "spun-bonded nonwoven" refers to material which is prepared by extruding a filament through a spinnerette onto a flat cooled surface in an irregular pattern to form a relatively uniform sheet which is not in a woven pattern. Spun-bonding requires adherence to a limited range of melt viscosities so that the roving spinnerettes can deliver the appropriate amount of material to the cooled surface. The detailed response of the polymer melt to the quenching is also a sensitive processing parameter. Such nonwoven materials typically have high strength characteristics and can be used for envelopes, towels, cloth wipes, fabrics, and other similar materials. The polymers of this invention can be optimized to meet the processing requirements by manipulation of many variables, including control of molecular weight and molecular weight distribution and selection of comonomers. Modifiers play an important role by facilitating the initial bonding among fibers, and the fiber pliability.

A further product type of the present invention includes adhesives. The polymer compositions of this invention have considerable utility as adhesives because they can be hot-melt or solvent-based products. Choice of comonomers and the molecular weight distribution can affect the melting point of the hot melt and its changes in morphology during tackifying and hardening. The modifiers can provide additional rheological and end-use properties to the hot melt formulations. In addition to optimizing viscosity, the modifiers can act as a trigger to initiate a gradual degradation process. The solvents to be used in the solvent-based adhesives can be a nonvolatile modifier part of the formulation. The food grade modifiers of this invention (e.g., acetyl triethyl citrate or lactide) can provide the functions of some solvent-based formulations obtained from toxic or flammable solvents.

The polymers of this invention that are to be used in adhesives range widely in composition and molecular weight, depending on the specific type of adhesive and the specific application. The surface properties of the substrates to be bonded are of great importance in the choice of polymer. For example, a polylactide ($M_w$ of about 200,000) was dissolved in a low boiling solvent and employed to bond together two pieces of wood. A strong bond was formed that lasted for more than two years at ambient temperatures in an office environment. Other substrates such as paper may need only $M_w$ of 10,000 to attain a strong bond. The excellent compatibility of polylactides and other polymers of this invention with substances with solubility parameters that differ widely among themselves indicates that these polymers are especially suited to bonding together disparate materials.

Adhesives of the present invention, typically are not transparent, have a weight average molecular weight of between about 5,000 to about 200,000; a $T_g$ of less than room temperature to 100° C., depending on end-use temperatures and whether they are structural or pressure-sensitive adhesives, can be rigid or flexible, and vary with respect to properties as mentioned previously in discussing laminating resins and film types.

A further material type of the present invention include various coatings. Unlike some films, moldings, and foams, coatings do not have to be strong enough to be self-supporting. Therefore, an extremely wide range of the polymer composition of this invention can be employed for coating use. The degradability aspect allows the coating to be a temporary protection of the underlying substrate against abrasion or other harm. The coating can serve many of the functions of a film, especially as a temporary printing surface so that the label of a container is among the first parts of a package to degrade.

The coating can serve as a binder to incorporate pigments onto writing papers. This type of usage can facilitate the degradation of the paper substrate by providing an acid environment for cellulose hydrolysis.

Generally, the polymers to be used on coatings can have a lower molecular weight and less crystallinity than those that are to be used in films. Thus, molecular weights may range from 10,000 to 100,000. However, in special circumstances, a combination of high molecular weight with a plasticizer can impart extra strength with pliability.

Although the materials of this invention are environmentally degradable, they also can be treated by other disposal systems. In particular, they can be incinerated in facilities that burn other plastic wastes. They also can be recycled with other thermoplastics by blending.

Additional information concerning suitable processes for preparing compositions of the present invention can be found in copending U.S. patent applications Nos. 07/579,005 filed on September on Sep. 6, 1990 by Sinclair and No. 07/579,465 by Sinclair filed on Sep. 6, 1990, the contents of which are incorporated herein as if set forth in full.

The following Examples are provided for purposes of illustration and are not intended to limit the scope of the invention.

EXAMPLES 1–3

These examples illustrate properties of copolymers produced from 80 percent by weight of L-lactide monomer and 20 percent by weight of racemic D,L-lactide monomer, which copolymers are modified with different amounts of residual monomer as a modifier additive, which result from different polymerization conditions, particularly with respect to temperature. Results are shown in Table 1.

In Example 1, 160 grams of L-lactide and 40 grams of racemic D,L-lactide, both of high purity (Purac, Inc., triply recrystallized), were charged into a 500 ml, round-bottom flask and purged with dry nitrogen overnight. 10 ml of stannous octoate is dissolved in 60 ml of anhydrous toluene, and 10 ml of the solvent was distilled to a Dean-Stark trap to effect dryness of this catalyst solution by azeotropic distillation. From the 10 ml of stannous octoate in 50 ml of dry toluene, a 0.20 ml portion was removed with a syringe and injected into the lactides in the reaction flask. The nitrogen purge was continuous via a syringe needle connection that enters the reaction flask through a rubber septum and vents via a piece of tubing that connects to a bubbler. The nitrogen flow was maintained at 1–3 bubbles per second. The flask was heated in an oil bath maintained at 123°–127° C. During the first part of the heating the lactides melt and are mixed thoroughly by swirling. Thereafter, the products become quite viscous. After 20 hours of heating, the flask and the colorless, transparent products were removed from the heating bath, cooled, the flask broken, and shocked with liquid nitrogen to remove glass from the product. The copolymer was molded in a heated hydraulic press. Compression molding to 5 to 10 mil thick films was possible at 20,000 psi pressure, at 170° C., in a time period of 2 minutes. The films were evaluated for their tensile properties on a Instron tester, and the results are listed in Table 1. Samples ⅛ inch thick were also molded for impact strength testing. A thermogravimetric analysis (TGA) of the product was performed, noting the weight loss upon heating the sample to 150° C. in 4 minutes and holding the temperature at 150° C. for 60 minutes. The weight loss of the sample was 19.5 percent and nearly complete in 60 minutes. The weight loss is attributed to loss of lactide monomer. Results of differential scanning calorimetry reveal that the composition has an endotherm beginning about 110° C., becoming more pronounced as the temperature increases to 200° C. No melting point was observed. Specimens were annealed at 185° F. overnight and reexamined. They remained transparent, colorless and pliable. Samples of the copolymer could be remolded 6 times without any discoloration or obvious loss of strength. Thin-films were clear, transparent, colorless, and quite flexible, despite the repeated molding.

TABLE 1

PROPERTIES OF COPOLYMERS[a] OF L-LACTIDE AND D,L-LACTIDE WHEN PLASTICIZED BY LACTIDE

| Example No. | 1 | 2 | 3 |
|---|---|---|---|
| Film thickness, mil | 8 | 8 | 10 |
| Tensile strength, 1000 psi, ASTM D638 | 3.9 | 1.7 | 7.9 |
| Elongation, percent | 28 | 806 | 3.5 |
| 100 percent modulus, 1000 psi | 0.74 | — | — |
| 200 percent modulus, 1000 psi | 1.20 | — | — |
| Tangent modulus, 1000 psi | 36.6 | — | 289 |
| Izod impact strength, ft-lb/in.[b] | 0.63 | — | 0.4 |
| $M_w$, 1000's | 540 | 281 | 341 |
| $M_n$, 1000's | 270 | 118 | 97.5 |
| Residual lactide, wt. %[c] | 19.5 | 27.8 | 2.7 |

[a] 80/20, weight ratio, of L-/racemic D,L-lactide.
[b] ⅛ inch, notched samples.
[c] By isothermal TGA weight loss at 150° C.

In Example 2, 1.84 Kg of L-lactide, 0.46 Kg of racemic D,L-lactide and 2.3 ml of the stannous octoate solution were charged into a 3-liter round-bottom flask. The mixture was purged with argon for 3 hours, then heated isothermally in a 125° C. oil bath. The mixture melted, was mixed thoroughly by swirling, and formed a homogeneous, transparent, colorless fluid whose viscosity increased substantially after several hours. After 64 hours the flask was removed from the heating bath, cooled, and the glass removed from the clear, transparent, solid product. The rubbery composition was guillotined into slices and ground to ⅛ inch, or smaller, in size using a grinder with dry ice. The grind was dried in an air circulating oven at 100° F. for several hours, then vacuum dried overnight at ambient temperature. Compression-molded films were prepared as described in Example 1 and the films were examined for their tensile properties and weight loss by TGA.

In Example 3, 79.98 g of L-lactide, 20.04 g of racemic D,L-lactide, and 0.20 ml of stannous octoate solution were charged into a 250-ml, round-bottom flask. The flask was swept by nitrogen through inlets and outlets and heated in a 125° C. oil bath. The mixture melted to a colorless fluid that was thoroughly mixed by swirling the flask. After 2 hours, the oil bath temperature was increased to 147° C., and after 14 hours total heating time, the temperature was decreased to 131° C.. Total heating time was 18 hours. The product is transparent, colorless, and glassy. It was evaluated, similar to Examples 1 and 2, and the results are recorded in Table 1.

EXAMPLE 4

This example demonstrates the degradability in water of the copolymer composition of Examples 1 and 3. Films of the copolymers of Examples 1 and 3 were immersed in water for several months. After 3 weeks, the copolymer of Example 1 became hazy while that of Example 3 remained clear for approximately 2 months; after 3 months the film of Example 3 became noticeably hazy and the film of Example 1 is white and opaque. The water that had been in contact with the film of Example 1 tastes acidic while that of Example 3 is tasteless.

EXAMPLES 5–10

These examples demonstrate the properties of copolymers produced from 90 percent by weight of L-lactide monomer and 10 percent by weight of racemic D, L-lactide monomer, which polymers are modified with varying amounts of lactide added to the copolymer by melt blending. Polymerization was not cut short to provide residual monomer as was the case with Examples 1 and 2.

A series of experiments were performed in which the copolymers of L- and racemic D,L-lactide were prepared, melt blended with variable amounts of lactide, and the physical properties of the blends evaluated as a function of the lactide composition. Monomer lactide content was assayed by an isothermal, thermogravimetric analysis. The lactide contents were measured before and after compounding and molding into films.

It was observed that open roll, 2 roll milling tended to volatilize the lactide at temperatures required for the very high molecular weight lactide copolymers. These losses could be minimized by masterbatching or by using lower molecular weight lactide copolymers (and their lower attendant mixing temperatures). A better mixing and blending method was a conventional, twin screw extruder, which minimized volatile losses. Some results are shown in Table 2.

TABLE 2

TENSILE PROPERTY COMPARISONS[a] OF PLASTICIZED COPOLYMERS OF L-LACTIDE AND D,L-LACTIDE[b]

| Ex. No. | Lactide (Wt. %) | Elastic Modulus (1000 psi) | 1% Secant Modulus (1000 psi) | Yield Strength (1000 psi) | Strain at Yield (%) | Break Strength (1000 psi) | Strain at Break (%) |
|---|---|---|---|---|---|---|---|
| 5 | 1.3 | 289 | 291 | — | — | 7.5 | 3 |
| 6 | 17.3 | 119 | 119 | 2.23 | 4 | 2.29 | 288 |
| 7 | 19.2 | 95.5 | 90.3 | 1.97 | 5 | 4.24 | 536 |
| 8 | 19.6 | 88.7 | 88.7 | 1.72 | 4 | 2.12 | 288 |
| 9 | 20.5 | 50.3 | 50.3 | 1.21 | 5 | 2.16 | 338 |
| 10 | 25.5 | 33.7 | 22.9 | 0.32 | 4 | 2.44 | 546 |

[a]ASTM 882; all samples were compression molded 5–10 mil films except Examples 13 and 14; strain rate 1.0 in/in min for all.
[b]90/10, weight ratio of L-/racemic D,L-lactide The results shown in Table 2 do not differ remarkably from the similar compositions of Examples 1 and 2, which were prepared by leaving residual monomer in the melt from polymerization. Those skilled in the art will recognize, however, that precise physical properties will vary somewhat depending on the intimacy of the mixture, the tensile testing conditions, and the fabrication technique for preparing the films. Comparisons from Table 2 reveal that the lactide-polymer mixtures have a broad range of controllable compositions that mimic many conventional, nondegradable plastic types.

The blends of polylactide and lactide plasticizer are quite pliable, becoming increasingly so with increasing lactide content. They are colorless and transparent. Only a very faint (pleasant) odor of lactide is detectable and no discernable taste of lactide is noticeable. The Table 2 plasticized film samples were tear resistant, easily foldable, and can be punctured without shattering or tearing. They stiffen somewhat when placed in a cooler (5° C., 40° F.), but remain flexible and creasible without breaking. These films noticeably soften in the hand, indicating a glass transition temperature below 37° C. When the lactide content is less than 20 percent, the films will have a rattle typical of a polyolefin film. At greater lactide contents the films have the drape and "warm" feel of a plasticized poly(vinyl chloride) (PVC). In fact, the compositions of the invention are also a replacement for plasticized PVC in many applications.

As shown in Table 2, the elastic moduli (initial tangent moduli) can be relatively high, similar to a linear low density polyethylene (LLDPE). This is an indication of potential form stability. Lower moduli and tensile strengths are similar to low density polyethylene (LDPE). At approximately 17–20 percent lactide content, the tensile properties are similar to polyethylenes used in trash bags and shopping bags. At lower lactide contents, the blends have a similarity to polypropylene.

EXAMPLE 11

This example illustrates a 90/10 L-/racemic D,L-lactide copolymer modified with oligomeric lactic acid and lactide additives, which modifiers were added to the composition separately at different temperatures. A 90/10, L-/D,L-lactide copolymer, analyzed by gel permeation chromatography to have a weight-average molecular weight of 480,000 and a number average molecular weight of 208,000, was banded, that is, melted and mixed on an open, 2-roll mill preheated to 350° F. The copolymer will not melt and band well on the mill below 350° F. To 25 grams of this melted copolymer was added 10 grams of oligomeric lactic acid of a degree of polymerization of 2.34. The temperature was then dropped to 300° F., where the mixing was still quite good. With the roll temperature at 300° F., 10 grams of L-lactide was added slowly and mixed. The mix was stripped from the roll and pressed into a thin film in a press at 300° F. The 5–10 mil thick film was colorless, transparent and very flexible. Without the lactide the resulting film would have been stiff. Without first adding the oligomeric lactic acid the lactide could not have been added on a mill without being lost to volatilization.

EXAMPLES 12–18

Examples 12–18 illustrate properties of a physical blend of 90/10, weight percent, L-lactide/racemic D,L-lactide copolymer and L-lactide homopolymer, modified by adding oligomeric polylactic acid.

In example 12, polymers of lactides were prepared by methods similar to Example 3. A 90/10, weight percent L-lactide/racemic D,L-lactide copolymer was melt polymerized using 0.02 parts per hundred, anhydrous stannous octoate catalyst. In a similar manner a 100 percent L-lactide homopolymer was prepared. The copolymer was melt blended with the homopolymer at 350° F. in a twin-screw extruder at a weight ratio of 90/10, copolymer/homopolymer. Gel permeation chromatography of the blend reveals a weight-average molecular weight ($M_w$) of 182,000 and a number-average molecular weight ($M_n$) of 83,000. Residual lactide monomer by thermogravimetric analysis was 1.7 weight percent. Properties of the polymer blend are shown in Table 3.

In Example 13, the polymer blend of Example 12 was then melt blended with oligomeric polylactic acid having an average degree of polymerization of 3.4 on an open, 2-roll mill for 20 minutes at 325° F. The mix was compression molded into films and tested for physical properties, the results of which are as shown in Table 3. The gel permeation chromatography molecular weights were smooth, monomodal distributions ($M_w/M_n$=2.6) with $M_w$=192,000 and $M_n$=73,000.

TABLE 3

PROPERTIES OF MELT BLENDS OF 90/10 POLYLACTIDES AND OLIGOMERIC POLYLACTIC ACID

| Example Number | Composition, wt. % | | Lactide, (wt. %) | Elastic Modulus (1000 psi)[a] | Break Strength, (psi)[a] | Strain at Break, (%)[a] | $T_g$, (°C.)[b] |
|---|---|---|---|---|---|---|---|
| | Polymer | Oligomer | | | | | |
| 12 | 100[c] | 0 | 1.7 | 298 | 7500 | 3 | 55 |
| 13 | 91[c] | 9[d] | 1.8 | 275 | 6113 | 2 | — |
| 14 | 100[e] | 0 | 1.6 | 308 | 7478 | 3 | 58 |
| 15 | 70[e] | 30[f] | 0.4 | 254 | 5052 | 3 | 42 |
| 16 | 60[e] | 40[f] | 0.0 | 202 | 3311 | 2 | 38 |
| 17 | 50[e] | 50[f] | 0.0 | 106 | 2334 | 25 | 35 |
| 18 | 40[e] | 60[f] | 0.0 | 36 | 1180 | 129 | 35 |

[a]ASTM 882; 5–10 mil, compression-molded films; strain rate 1.0 in./in./min.
[b]Glass transition temperature by differential scanning calorimetry.
[c]A blend of 90% of a 90/10 L-lactide/racemic D,L-lactide copolymer with 10% poly L-lactide homopolymer.
[d]Oligomeric polylactic acid with 3.4 degree of polymerization.
[e]A blend of 80% of a 90/10 L-lactide/D,L-lactide copolymer with 20% poly L-lactide homopolymer.
[f]Oligomeric polylactic acid with 4.3 degree of polymerization.

In Example 14, the 90/10, weight ratio, L-lactide/racemic D,L-lactide copolymer of Example 12 was melt blended with 20 percent of the poly L-lactide homopolymer, also of Example 12. Physical properties of the polymer blend of Example 14 are shown in Table 3. The blend of Example 14 was, in turn, melt blended with various amounts of the oligomeric polylactic acid having an average degree of polymerization of 4.3 and the resulting blends were tested as before and physical properties are shown in Table 3 as Examples 15–18. Table 4 shows the gel permeation chromatography molecular weights and glass transition temperatures of the compositions of Examples 14–18.

prepared by dissolving 20 g in 110 ml of toluene, previously dried over molecular sieves, then distilling 10 ml toluene in order to azeotropically dry the solution. The final concentration was 0.2 g/ml stannous octoate in toluene. A 0.3 ml quantity of the stannous octoate solution was injected through the septum onto the L-lactide. The flask and its contents were placed in a 150° C. oil bath, and when melted, swirled vigorously to obtain a homogeneous mix. The argon purge continued and a thermocouple was fitted through the septum into the melt. The melt was 143° C. The temperature of the oil bath was advanced to 200° C. and heating and a slight argon purge continued for 20 hours. The temperature

TABLE 4

MOLECULAR WEIGHTS AND GLASS TRANSITION TEMPERATURES OF 90/10 POLYLACTIDES AND OLIGOMERIC POLYLACTIC ACID

| Example Number | Composition (wt. %) | | Residual[a] Monomer, (%) | GPC × 10$^{-3}$ [b] | | | | $T_g$, (°C.)[c] |
|---|---|---|---|---|---|---|---|---|
| | Copolymer | Oligomer | | $M_n$ | $M_w$ | $M_z$ | $M_w/M_n$ | |
| 14 | 100[d] | 0 | 1.6 | 76 | 175 | 410 | 2.3 | 58 |
| 15 | 70[d] | 30[e] | 0.4 | 67[f] | 136 | 299 | 2.0 | 42 |
| 16 | 60[d] | 40[e] | 0.0 | 61[f] | 112 | 211 | 1.8 | 38 |
| 17 | 50[d] | 50[e] | 0.0 | 62[f] | 114 | 223 | 1.8 | 35 |
| 18 | 40[d] | 60[e] | 0.0 | 69[f] | 120 | 207 | 1.7 | 35 |

[a]Residual monomer by thermogravimetric analysis.
[b]Molecular weight by gel permeation chromatography.
[c]Glass transition temperature by differential scanning calorimetry.
[d]A blend of 80% of 90/10, L-lactide/racemic D,L-lactide copolymer with 20% poly L-lactide homopolymer.
[e]Oligomeric polylactic acid with 4.3 degree of polymerization.
[f]After blending; melt-blending on an open mill roll at 325° F.

EXAMPLES 19–28

Examples 19–28 illustrate the incorporation of lactide modifier in conjunction with quenching to obtain pliability and transparency in compositions containing poly L-lactide homopolymer. Alternatively, the polymers can be annealed to improve stability against heat distortion. Results of these examples are shown in Table 5.

In Example 19, poly L-lactide was first prepared. Thus, 300 g of triply recrystallized and thoroughly dried L-lactide was loaded into a clean, flame-dried, argon-cooled, 500 ml round-bottom flask. The flask was fitted with a rubber septum and inlet and outlet syringe needles that admitted a continuous argon purge. Stannous octoate solution was of the melt advanced to 170°–174° C. in the first two hours of heating. The final temperature was 170° C. After 20 hours of heating the flask was cooled in air to room temperature. The solid polymer was transparent.

Polymer was recovered by shocking the flask with dry ice to free it from the glass. The residual monomer was analyzed by thermogravimetric analysis and molecular weights were determined by gel permeation chromatography. Differential scanning calorimetry reveals a glass transition temperature ($T_g$) at 53 degrees and two melting point endotherms with peaks at approximately 170° and 190° C. The gel permeation chromatography molecular weights were determined to be: $M_n$=129,000; $M_w$=268,000; $M_z$=462,000; and $M_w/M_n$=2.08. Residual monomer by thermogravimetric analysis was 2.3 percent. The experiment shows that L-lactide can be polymerized above, or near, its melting point and the products remain transparent and more amorphous.

elevated temperatures will restore crystallinity to amorphous samples.

TABLE 5

POLYMERIZATION OF L-LACTIDE

| Ex. No. | Catalyst Amount (pph) | Temp (°C.) | Time (hours) | Polymer Appearance | Residual Monomer (percent) | Sample Size (g) |
|---|---|---|---|---|---|---|
| 19 | 0.02 | 156–201[a] 150–174[b] | 20 | clear transparent, hard, glassy | 2.30 | 300 |
| 20 | 0.02 | 155–165[a] | 72 | crystalline, opaque, hard, brittle | — | 104 |
| 21 | 0.005 | 120–200[a] 111–200[b] | 24 | crystalline, opaque, hard, brittle | — | 100 |
| 22 | 0.02 | 135–145[a] 135–152[b] | 22 | crystalline,[d] opaque, hard, brittle | 1.1 | 500 |
| 23 | 0.02 | 117–185[a] 120–175[b,c] | 24 | crystalline, opaque, hard, brittle | 1.74 | 100 |
| 24 | 0.02 | 160–170[a] | 8 | crystalline, opaque, hard, brittle | 2.18 | 2,000 |
| 25 | 0.02 | 145[a] 137–144[b] | 15 | crystalline, opaque, hard, brittle | 3.6 | 25 |
| 26 | 0.0553 | 190[a] 160–215[b] | 0.3 | clear, pliable, tough, transparent | 10.1 | 25 |
| 27 | 0.0553 | 188–193[a] 147–200[b] | 0.28 | clear, transparent, pliable except at edge of polymerizate | 22.9 | 25 |
| 28 | 0.02 | 145[a] 150–133[b] | 2.75 | crystalline,[d] opaque, hard, brittle | 52.5 | 25 |

[a]Oil bath temperature.
[b]Polymer melt temperature.
[c]This polymer crystallized at 160–169° as the temperature was advanced and it did not remelt.
[d]Transparent at reaction temperature, crystallizes upon cooling.

In Example 20, by methods similar to Example 19, 104.0 g of L-lactide was polymerized using 0.10 ml of stannous octoate catalyst solution. However, the reaction temperatures were 155°–165° C. for 72 hours. The polymer slowly crystallized upon forming and was a white opaque solid at reaction or room temperature. Since the sample was smaller than the preceding experiment the polymer cooled more quickly, but it did not quench to a transparent solid. In comparison to Example 19, the lower reaction temperature permits the poly L-lactide to crystallize and become opaque, thus an intimate dispersion of plasticizer does not form.

The temperature was slowly advanced in many of the experiments to accommodate the polymerization exotherm. The reaction temperature must reach at least 170°–175° C. before there is substantial monomer-to-polymer conversion, otherwise the poly(L-lactide) crystallizes and is difficult to remelt.

In Examples 21–28 the polymerization of L-lactide was repeated varying the conditions to obtain poly L-lactides with different residual lactide contents and crystallinities. The results are shown in Table 5. Table 5 shows that pliability and toughness were obtained only when the product was quenched from the melt, was transparent at room temperature, and contained approximately 10 percent or more residual lactide. It is believed that the L-lactide homopolymer must be polymerized in the melt, and quenched from the monomer-polymer melt temperatures, to a transparent material as evidence of its homogeneous and intimately plasticized properties. When the poly L-lactide crystallizes during polymerization because the polymerization temperature is well below the polymer's melting point, the residual monomer modifier is no longer effective as a plasticizer. If the polymer crystallizes upon cooling to room temperature, it also loses its plasticization. Annealing at

EXAMPLES 29–33

Examples 29–33 illustrate that transparency and intimacy of association between copolymer and monomeric modifier for L-lactide/racemic D,L-lactide copolymers is affected by the ratio of L-lactide/D,L lactide in the copolymer. At approximately 95/5, weight ratio, the copolymer easily quenches to a transparent solid. At a weight ratio of 90/10, the copolymer quenches quite easily. The 100 percent L-lactide polymer quenches with difficulty from thick sections of the polymer to a transparent material. Some comparisons are shown by Examples 29–33 in Table 6 for varying weight ratios of L-lactide/racemic D,L-lactide. Thinner cross sections, i.e., films-of the L-lactide polymer can be plasticized with monomeric modifiers and quenched to pliable and transparent materials. The 80/20 copolymer quenches very easily to a transparent solid. The latter has only a trace of crystallinity as seen by differential scanning calorimetry.

TABLE 6

TRANSPARENCY OF L-LACTIDE/ RACEMIC D,L LACTIDE COPOLYMERS

| Ex. No. | Lactide L/D,L Wt. Ratio | Temp., °C.[a] | Time, hours | O/T[b] | GPC $M_w$ | Residual Monomer, percent |
|---|---|---|---|---|---|---|
| 29 | 95/5 | 145–160 | 67 | SO | 385,000 | 2.64 |
| 30 | 100/0 | 135–152 | 22 | O | 322,000 | 1.1 |
| 31 | 90/10 | 150–157 | 45 | T | 821,000 | 4.95 |
| 32 | 90/10 | 150–170 | 48 | T | 278,000 | 1.37 |
| 33 | 80/20 | 135–175[c] | 23 | T | — | — |

[a]Melt temperature (polymerization temperature).

TABLE 6-continued

TRANSPARENCY OF L-LACTIDE/ RACEMIC D,L LACTIDE COPOLYMERS

| Ex. No. | Lactide L/D,L Wt. Ratio | Temp., °C.[a] | Time, hours | O/T[b] | GPC $M_w$ | Residual Monomer, percent |
|---|---|---|---|---|---|---|

[b]Opaqueness/Transparency (O/T) after air-cooling of polymerizates; opaque (O), slightly opaque (SO), transparent (T).
[c]Slow-cooled for 1 hour.

All of the lactide polymers thermoform easily, that is, when heated by a radiant heater until soft, then sucked down on an intricate mold, they all form the pattern of the mold easily. However, the poly L-lactide becomes partially cloudy and hazy upon cooling. The 95/5, 90/10, and 80/20 copolymers are quite clear and transparent throughout their thermoforms.

EXAMPLES 34–39

Examples 34–39 illustrate the beneficial effects of adding lactide as a modifier during compounding of a L-lactide/racemic D,L-lactide copolymer. The examples show that without lactide as modifier, the lactide polymer degrades during compounding. With the addition of lactide both discoloration and molecular weight decrease are prevented or substantially reduced during compounding.

In Example 34, a 90/10, L-lactide/D,L-lactide copolymer, prepared as described by previous methods using 0.02 pph $SnCl_2 \cdot 2H_2O$ catalyst, was ground and extruded into pellets from a twin screw compounder, adding 5 weight percent lactide. The melt zone temperature of the extruder rose to 390° F., the polymer discolored, and the weight average molecular weight ($M_w$, by gel permeation chromatography) decreased by approximately 40 percent. The results indicate that insufficient lactide was added for this very high $M_w$ copolymer. The results are shown in Table 7.

In Example 36, the compounded pellets from Example 34 were recompounded adding a further 10 weight percent lactide. The melt zone temperature was 375° F., and the results were much better. Further discoloration did not occur, molecular weight decreased slightly, or within experimental error, and a pliable composition was obtained.

TABLE 7

EFFECT OF LACTIDE AS MODIFIER DURING COMPOUNDING

| Ex. No. | Color | $M_w$[a] | $M_w/M_n$[a] | Lactide[b] weight percent |
|---|---|---|---|---|
| | | Before Compounding | | |
| 34 | light yellow | 513 | 2.15 | 0.78 |
| 35 | light yellow | 278 | 1.80 | 1.37 |
| | | After Compounding | | |
| 34 | dark yellow | 322 | 2.05 | 5.56[c] |
| 35 | yellow | 184 | 1.90 | 2.26 |
| 36 | dark yellow | 307 | 2.00 | 14.4[d] |
| 37 | colorless[e] | 324 | 1.99 | 14.6 |

[a]From GPC, × 10⁻³.
[b]By thermogravimetric analysis, at 200° C.
[c]Five weight percent lactide added during compounding.
[d]Further 10 weight percent lactide added during compounding.
[e]Thin film.

In Example 35, to ascertain that the second compounding and extrusion were facilitated due to the lactide modifier and not the decreased molecular weight, another compounding was performed starting with a similar $M_w$ copolymer of 90/10, L-lactide/racemic D,L-lactide. In this case, no lactide was added back in during the compounding. The melt zone temperature was 382° F., the copolymer was discolored, and the $M_w$ decreased by approximately 66 percent. In addition, approximately 5 percent more torque was required to compound the mix of $M_w$ 278,000 as compared to the one of $M_w$ of 322,000 with added lactide.

After compounding twice with lactide, Example 36 was analyzed by thermogravimetric analysis and found to have a lactide content of 14.4 percent. The material of Example 36 was converted to a blown film by means of a Haake-Brabender extruder in Example 37. Thin films of this composition are colorless, highly transparent, and very pliable and extensible. The $M_w$ by gel permeation chromatography was 324,000 (cf. $M_w$=307,000 before compounding and extrusion). The $T_g$ of this plasticized material is 42° C. and differential scanning calorimetry reveals a very small amount of crystallinity melting at approximately 138° C. The amount of lactide present is 14.6 weight percent as estimated by thermogravimetric analysis.

The compounded polylactides, Example 34 and 35, were mixed together in the twin-screw compounder with extra lactide to raise the lactide level to approximately 20 percent producing the compounds of Examples 38 and 39. The compounding temperature was 347° F. (175° C.), much reduced from the previous 375° to 385° F. The compounding proceeded smoothly without further discoloration.

The above results clearly show the beneficial effects of added lactide as modifier. The required torque to compound the compositions, the discoloration, and the working temperature are decreased when adding lactide. Further evidence of plasticization is seen in the lowered $T_g$ and the pliability of the compositions. In addition, molecular weight decreases are avoided and stable compositions are obtained. It will be obvious to those skilled in the art that the amount of lactide employed depends on many factors, including the desired amount of plasticization sought, the type of compounder that is used, and the molecular weight of the polylactides.

EXAMPLES 40 and 41

Examples 40 and 41 illustrate blown film extrusion of polylactides. These pliable films mimic polyolefins. The plasticized compounds of Examples 38 and 39 were adjusted to approximately 20 percent lactide in the twin-screw extruder. They were converted to blown films using a Haake-Brabender extruder. This consists of a ¾-inch extruder with a blown-film die and take-up device. The blown-film was achieved using a 12.7 mm outside diameter orifice and a pin to establish an extrusion gap of 0.483 mm. An extrudate temperature of 187° C. was maintained. A stable bubble was blown at this temperature with the inflation air at 3 oz/in² gauge pressure. Cooling air was blown against the exterior of the bubble at 18 psi. Since the final average film thickness was 0.158 mm (6.2 mil), the blow-up ratio was 3:1. When the extruder gap was reduced from 0,483 to 0.254 mm, or the temperature raised, the polymer cooled too quickly to form a crystalline, cloudy extrudate that would not expand. The larger orifice die produced an extrudate that was thicker and more viscous, cooled more slowly, and expanded in a consistent manner. The extruded film exhibited some elastic memory when stretched. The film also was resistant to tear and puncture and was very difficult to break by stretching. The blown film had an average elastic modulus of 117,000 psi, an average tensile strength of 3,735 psi, and an average elongation to break of 370 percent. This modulus is slightly higher than that of linear low density polyethylene, but the strength and elongation to break are comparable. The Elmerdorf Tear Strength (ASTM 1922) was 424 g in the cross machine direction and 183 g in the machine direction. The $T_g$ of the material was 36° C., $M_w$ by gel permeation chromatography was 229,000, the residual lactide by thermogravimetric analysis was 19.7 percent, and the differential scanning calorimetry curves showed a weak endotherm centered at approximately 135° C.

EXAMPLES 42–46

Examples 42–46 illustrate modification with oligomeric esters of polylactic acid. Copolymers of 90/10 L-lactide/racemic D,L-lactide were melt blended-with added lactide, esters of oligomeric lactic acid, and mixtures thereof. They were characterized by tensile and thermal properties.

In Example 42, a control copolymer of 90/10, L-lactide/racemic D,L-lactide was assayed by thermogravimetric analysis to be 6.74 percent lactide. This was mixed with 30 percent by weight oligomeric polymethyllactate (Mella) in Example 43, which was prepared by heating 2,500 g of (S)-methyllactate in an autoclave at 210° C. for 3 hours, then collecting the Mella which fractionally distilled at 81° to 85° C. at a pressure of 1.25 torr. The mixture was melt blended on an open 2-roll mill at approximately 350° F. The blend was compression molded in a press at approximately 350° F. into clear, pliable films. The tensile properties, before and after, adding the Mella are recorded in Table 8. The glass transition temperature ($T_g$) was reduced by the Mella modifier.

In Example 44, the 90/10, L-lactide/racemic D,L-lactide copolymer was melt blended with added L-lactide in a twin screw extruder to adjust the L-lactide content to 20 percent by weight. In Example 45, the blend was further mixed with oligomeric polyethyllactate (Ella). In Example 46, the blend was mixed with Mella. The properties of these blends are also recorded in Table 8.

TABLE 8

CHARACTERISTICS OF POLYLACTIDES[a] PLASTICIZED WITH OLIGOMERIC ESTERS OF LACTIC ACID

| Ex. No. | Plasticizer | Elastic Modulus psi | Break Strength psi | Strain at Break, % | $T_g$[b] | $T_m$[c] |
|---|---|---|---|---|---|---|
| 42 | 6.74%[d] L-lactide | 370,000 | 6,903 | 2 | 51 | 141 |
| 43 | 6.74%[d] L-lactide and 30% Mella[e] | 154,000 | 2,012 | 100 | 30 | 141 |
| 44 | 20% L-lactide | 101,000 | 2,637 | 278 | — | — |
| 45 | 20% L-lactide and 30% Ella[f] | 7,316 | 2,561 | 339 | — | — |
| 46 | 20% L-lactide and 30% Mella[e] | 3,620 | 495 | 83 | — | — |

[a] 90/10, L-lactide/racemic D,L-lactide copolymer.
[b] Glass transition temperature.
[c] Melting point.
[d] Analyzed by thermogravimetric analysis.
[e] Methyl lactate oligomer.
[f] Ethyl lactate oligomer.

EXAMPLES 47–57

Examples 47–57 illustrate increasing the melting point of L-lactide/racemic D,L-lactide copolymers by increasing the amount of L-lactide comonomer. The procedures of Example 1 were repeated except that the ratio of L- and racemic D,L-lactide were changed as shown in Table 9. The pure L-lactide polymer, Example 52, would not always mold well at 170°–200° C. since it frequently crazed badly on cooling in the mold. Frequently, on cooling, it opacified. Not shown in Table 9 is the fact that as the amount of L-lactide comonomer increases, so does the percent crystallinity and the ease of crystallization.

TABLE 9

PROPERTIES OF L-LACTIDE/RACEMIC D,L-LACTIDE COPOLYMERS

| Composition, Weight Ratio, L-Lactide/ D,L-Lactide (Racemic) | 80/20 | 85/15 | 87.5/12.5 | 90/10 | 90/10 | 95/5 | 100/0 |
|---|---|---|---|---|---|---|---|
| Example No. | 1 | 47 | 48 | 49 | 50 | 51 | 52 |
| Color/Transparency | colorless & transparent | → | → | → | → | → | white, opaque |
| Film Thickness, mil | 10 | 5 | 15 | 11 | 5 | 10 | 5 |
| Tensile Strength, 1000 psi, ASTM D882 | 7.9 | 6.9 | 8.3 | 8.6 | 8.2 | 9.2 | (a) |
| Elongation, % | 3.5 | 5.8 | 6.0 | 7.1 | 7.2 | 5.1 | (a) |
| Tangent modulus, 1000 psi | 289 | 221 | — | 210 | 268 | — | — |
| Izod impact strength[b], ft-lb/in. | — | 0.44 | 0.34 | 0.31 | — | 0.41 | (a) |
| $M_w$, 1000's | — | 928 | — | — | — | — | — |
| $M_n$, 1000's | — | 218 | — | — | — | — | — |
| $T_g$, C[c] | 53 | 53 | 48 | 44 | — | 46 | — |
| $T_m$, C[c] | — | — | 125 | 133 | — | 152 | 190 |

[a] Crazes on cooling, too brittle to test.
[b] Notched samples, impacted on notched side on ⅛ in. thick specimens.
[c] Differential scanning calorimetry in nitrogen with 10° C./min. heating rate.

In Example 53, similar to Examples 49 and 50, a 90/10 weight ratio copolymer of L-lactide/racemic D,L-lactide was prepared. Into a dry, nitrogen-swept, 2-liter flask was placed 1045.8 g L-lactide and 116.4 g of racemic D,L-lactide. A 1.0 ml quantity of anhydrous stannous octoate (0.2 ml per ml of toluene) solution was added. The flask was swept with nitrogen overnight, then heated in a 141° C. oil bath until the monomers are melted and well mixed, and the heating decreased slowly to 125° C. and continued for 72 hours. The polymer slowly whitens on cooling. After removing the glass, the cloudy, colorless, glassy copolymer was evaluated. Gel permeation chromatography obtains a weight-average molecular weight ($M_w$) of 522,000, and a number-average molecular weight ($M_n$) of 149,000.

A DSC of the lactide polymer reveals a strong melting temperature at 145° C.. The lactide polymer was melted, quenched, and examined again by DSC to reveal no crystallization or melting points. However, a $T_g$ appears at approximately 50°–55° C.. The results show the polymer can be crystalline or amorphous, depending on its heat history.

The composition series was extended in Examples 54–57, as shown in Table 10, using the procedures of Example 1 except other L-lactide and racemic D,L-lactide ratios were used and heating was 2 hours 125° C., 14 hours 125°–147° C., then 2 hours 147°–131° C. The results are shown in Table 10.

TABLE 10

TENSILE AND MODULUS PROPERTIES OF L-LACTIDE AND D,L-LACTIDE COPOLYMERS

| Composition, weight Ratio, L-Lactide/ D,L-Lactide (Racemic) | 70/30 | 60/40 | 20/80 | 0/100 |
|---|---|---|---|---|
| Example No. | 54 | 55 | 56 | 57 |
| Color/transparency | Colorless/clear | → | → | → |
| Film thickness, mil | 6–9 | 4–6 | 4–5 | 5–7 |
| Tensile strength,[a] 1000 psi, ASTM D638[a] | 6.9 | 6.7 | 5.8 | 5.6 |
| Elongation, % | 3.2 | 3.0 | 2.7 | 2.8 |
| Tangent modulus, 1000 psi | 287 | 293 | 275 | 278 |

[a] Films were pulled at a jaw separation of 0.2"/min. and chart speed of 5"/min.

EXAMPLES 58–61

Examples 58–61 illustrate various polymer/modifier compositions of the present invention and the physical properties thereof wherein the polymer is a 50/50 weight ratio copolymer of L-lactide/glycolide.

In Example 58, a 50/50 weight ratio copolymer of L-lactide/glycolide was prepared from 750 g of each monomer. These were mixed thoroughly in a melt with 0.3 g of stannous chloride dihydrate, as a catalyst, in a 120° C. oil bath, then heated to 173° C. over 4 hours, then further heated overnight, before cooling and reducing the copolymer to pieces with a clean band saw and granulator. The copolymer was melted into a band on an open, two-roll mill heated to 330° F., and mixed for 15 minutes to volatilize and thereby remove residual monomer. The copolymer was pressed into 5 to 10 mil films by compression molding at 330° F. An isothermal thermal gravimetric analysis (TGA) of the film revealed 2.0 weight percent residual monomers. The film was transparent and colorless. The solubility parameter of the copolymer is about 10.5 cal/cm³.

In Examples 59–61, various compounds, as shown in Table 11, were used as modifiers with the copolymer of Example 58. The polymer was blended and mixed at 330° F. on an open, two roll mill for 10 to 15 minutes, then the modifier was added. The mixtures were then pressed into 5 to 8 mil films, for physical property measurements, the results of which properties are shown in Table 12.

TABLE 11

COMPATIBILITY OF 50/50 L-LACTIDE/GLYCOLIDE COPOLYMER WITH MODIFIERS

| Example No. | Additive | Percent Modifier | Solubility Parameter (cal/cc) | Modifier Compatible |
|---|---|---|---|---|
| 58 | None | 2.0(a) | 10.5 | — |
| 59 | Dimethyl adipate | 9.4 | 9.64 | yes |
| 60 | ε-Caprolactone | 9.8 | 10.1 | yes |
| 61 | Acetyl tributyl citrate | 7.4 | 9.0–9.4 | yes |

(a)Residual monomer.

TABLE 12

PHYSICAL PROPERTIES OF 50/50 L-LACTIDE/GLYCOLIDE COPOLYMER COMPOSITIONS

| Example No. | Tensile Yield Strength (1000 psi) | Strain at Yield (percent) | Elastic Modulus (1000 psi) | Break Strength (1000 psi) | Strain at Break (percent) | Plasticization by Modifier |
|---|---|---|---|---|---|---|
| 58 | (a) | (a) | 251. | 7.77 | 4 | — |
| 59 | (a) | (a) | 8.79 | 1.27 | 191 | good |
| 60 | (a) | (a) | 0.426 | 0.071 | 945 | good |
| 61 | 4.210 | 4 | 159. | 2.46 | 108 | good |

(a) No yield point.

As shown in Table 11, dimethyl adipate and ε-caprolactone each have a solubility parameter within the preferred range of about 1 cal/cm$^3$ and are compatible modifiers for use with the 50/50 L-lactide/glycolide polymer according to the present invention. Although the solubility parameter of acetyl tributyl citrate is slightly outside of the preferred range, acetyl tributyl citrate is compatible due to chemical groupings, in the form of ester linkages, having significant polarity present in the molecular structure. All of these modifiers performed well as plasticizers, as shown in Table 12.

EXAMPLES 62–87

Examples 62–90 illustrate the use of various modifiers with a 90/10 weight ratio copolymer of L-lactide/racemic D,L-lactide.

In Example 62, a 90/10 copolymer of L-lactide/D,L-lactide was prepared by methods similar to the polymerization in Example 58. Colorless, transparent films of the copolymer were compression molded at 330° F. The $T_g$ of the copolymer was 60° C. as measured by programmed TGA. Residual monomer of the films was zero percent by isothermal TGA. The copolymer had a solubility parameter of 9.59 cal/cm$^3$. The copolymer was quite stiff and the tensile properties are listed in Table 14.

In Examples 63–81, various compounds, as shown in Table 13, were used as modifiers for the copolymer of Example 62. All of the modifiers used in Examples 63–79 except Examples 71–75 have solubility parameters within the preferred range of from about 1 cal/cm$^3$ less than to about 1 cal/cm$^3$ greater than the solubility parameter of the copolymer. All compositions were prepared by blending at 330° F. on an open two roll mill, as in Examples 59–61. The mixtures were then pressed into films of 6–12 mils thickness for physical property measurements, the results of which are shown in Table 14. Examples 73 and 74 did not fuse completely on the mill at 330° or 380° F.

As seen in Table 13, all of these modifiers are somewhat compatible with the 90/10 L-lactide/D,L-lactide copolymer except for decahydronaphthalene, which is a highly nonpolar molecule. This lack of polarity may have resulted in noncompatibility even though a modifier is within the preferred range of solubility parameters. Stearoyl lactyllactic acid (Example 80) is somewhat compatible with the polymer, but exhibits some cloudiness, which is not preferred.

Table 14 shows that all of these modifiers, except for decahydronaphthalene and stearoyl lactyllactic acid, can be used as plasticizers. The lactic acid oligomers of Examples 77 and 78, although compatible, are only fair plasticizers because of their relatively high molecular weights. These higher molecular weight plasticizers, however, are highly useful for lowering the melt temperatures and glass transition temperatures of the composition, allowing efficient melt processing, and thereby also allowing incorporation of lower molecular weight plasticizers into the composition without detrimental volatilization.

TABLE 13

COMPATIBILITY OF 90/10 L-LACTIDE/D,L-LACTIDE COPOLYMER COMPOSITIONS WITH MODIFIERS HAVING SOLUBILITY PARAMETERS WITHIN PREFERRED RANGE

| Example No. | Additive | Weight Percent Additive | Modifier Solubility Parameter (cal/cc) | Additive Compatible |
|---|---|---|---|---|
| 62 | None | 0 | 9.59(a) | |
| 63 | Dimethyl adipate | 23.5 | 9.64 | yes |
| 64 | E-Caprolactone | 16.8 | 10.1 | yes |
| 65 | Diethyl adipate | 22.0 | 9.19 | yes |
| 66 | Triethyl citrate | 24.4 | 9.56 | yes |
| 67 | Acetyl tributyl citrate | 15.2 | 9.0–9.4 | yes |

TABLE 13-continued

COMPATIBILITY OF 90/10 L-LACTIDE/D,L-LACTIDE COPOLYMER
COMPOSITIONS WITH MODIFIERS HAVING
SOLUBILITY PARAMETERS WITHIN PREFERRED RANGE

| Example No. | Additive | Weight Percent Additive | Modifier Solubility Parameter (cal/cc) | Additive Compatible |
|---|---|---|---|---|
| 68 | Acetyl triethyl citrate | 22.2 | 9.51 | yes |
| 69 | Santicizer 409[b] | 10–20 | 9.35 | yes |
| 70 | Santicizer 412[b] | 10–20 | 9.34 | yes |
| 76 | Decahydronaphthalene | 15 | 8.8 | no |
| 77 | $L_{20}A$ at 330° F.[c] | 30.0 | 9.6 | yes |
| 78 | $L_{20}A$ at 300° F.[c] | 30.0 | 9.6 | yes |
| 79 | Dimethyl Phthalate | 22.0 | 10.45 | yes |
| 80 | Stearoyl lactyllactic acid | 20.0 | 8.91 | somewhat |
| 81 | Undecyl cyanide (Lauronitrile) | 30.0 | 8.93 | yes |

[a] Copolymer.
[b] Adipic acid polyesters.
[c] Oligomeric lactic acid with degree of polymerization of 20.

TABLE 14

PHYSICAL PROPERTIES OF 90/10 L-LACTIDE/D,L-LACTIDE
COPOLYMER COMPOSITION WITH MODIFIERS IN
PREFERRED SOLUBILITY PARAMETER RANGE

| Example No. | Tensile Yield Strength (1000 psi) | Strain at Yield (Percent) | Elastic Modulus (1000 psi) | Break Strength (1000 psi) | Strain at Break (percent) | Plasticization by Additive |
|---|---|---|---|---|---|---|
| 62 | (a) | (a) | 255. | 8.43 | 4 | |
| 63 | (a) | (a) | 8.28 | 1.79 | 452 | good |
| 64 | (a) | (a) | 12.6 | 1.90 | 307 | good |
| 65 | (a) | (a) | 10.5 | 1.76 | 287 | good |
| 66 | (a) | (a) | 9.50 | 2.55 | 444 | good |
| 67 | (a) | (a) | 21.0 | 2.48 | 306 | good |
| 68 | (a) | (a) | 1.55 | 1.58 | 457 | good |
| 69 | 4.87 | 4 | 185. | 3.51 | 378 | good |
| 70 | 1.50 | 8 | 67.4 | 2.82 | 247 | good |
| 76 | (a) | (a) | 340. | 5.91 | 4 | poor |
| 77 | (a) | (a) | 299. | 2.73 | 3 | fair |
| 78 | (a) | (a) | 346. | 6.46 | 4 | fair |
| 79 | 3.10 | 55 | 181. | 2.90 | 187 | good |
| 80 | 1.70 | 1 | 271. | 4.10 | 5 | <fair |
| 81 | 2.67 | 30 | 159. | 2.59 | 101 | fair |

(a) No yield point.

In Examples 82–85 Table 15, various compounds with solubility parameters below the preferred 1 cal/cm³ range were tested for use as modifiers for the 90/10 L-lactide/D,L-lactide copolymer of Example 62. The compounds used in these examples all exhibit little polarity and contained, at most, only weak polar chemical groupings in their molecular structures. These compounds were blended with the copolymer as previously described for Examples 63–81, except for di-t-butyl peroxide. Because di-t-butyl peroxide is normally liquid, its compatibility was noted from a presoak of the copolymer in an excess of that modifier both at 25° C. and 110° C. No swelling was observed, and this experiment was terminated without determination of physical properties. The other mixtures were pressed into films of 5–10 mils thickness for physical property measurements, the results of which are shown in Table 16 which shows that none of these compounds are compatible with the 90/10 L-lactide/D,L-lactide copolymer and thus are not suitable for use as modifiers. Table 16 shows that all of these compounds are poor plasticizers.

TABLE 15

COMPATIBILITY OF 90/10 L-LACTIDE/D,L-LACTIDE
COPOLYMER COMPOSITIONS WITH MODIFIERS
HAVING SOLUBILITY PARAMETERS OUTSIDE
PREFERRED RANGE AND HAVING LOW POLARITY

| Example No. | Additive | Percent Additive | Solubility Parameter (cal/cc) | Additive Compatible |
|---|---|---|---|---|
| 62 | None | 0 | 9.59 | — |
| 82 | Dodecylbenzene | 20 | 8.35 | no |
| 83 | Mineral oil | 30 | 8 | no |
| 84 | di-t-butyl peroxide | gross excess | 6.82 | no |

TABLE 16

PHYSICAL PROPERTIES OF 90/10 L-LACTIDE/D,L-LACTIDE COPOLYMER COMPOSITION WITH MODIFIERS OUTSIDE PREFERRED SOLUBILITY PARAMETER RANGE AND HAVING LOW POLARITY

| Example No. | Tensile Yield Strength (1000 psi) | Strain at Yield (Percent) | Elastic Modulus (1000 psi) | Break Strength (1000 psi) | Strain at Break (percent) | Plasticization by Additive |
|---|---|---|---|---|---|---|
| 62 | (a) | (a) | 255 | 8.43 | 4 | — |
| 82 | (a) | (a) | 341 | 4.79 | 6 | poor |
| 83 | | | (Could not mix) | | | poor |
| 84 | | | (Could not mix) | | | poor |

(a) No yield point.

In Examples 71–75 and 85–87, various compounds with solubility parameters above the preferred 1 cal/cm$^3$ range were tested for use as modifiers for the 90/10 L-lactide/D, L-lactide copolymer of Example 62 (Table 17). The compounds used in these examples contain significantly polar chemical groupings in their molecular structures. These compounds were blended with the copolymers as previously described for Examples 63–81. The mixtures were pressed into films of 5–10 mils thickness for physical property measurements, the results of which are shown in Table 18.

Most of the modifiers shown in Table 18 plasticize the 90/10 L-lactide/D,L-lactide copolymer, as determined by the reduction in modulus and increase in strain at break. The oligomeric glycolic acids of Examples 73–75 have a limited compatibility and do not mix easily with the copolymer.

TABLE 17

COMPATIBILITY OF 90/10 L-LACTIDE/D,L-LACTIDE COPOLYMER COMPOSITIONS WITH MODIFIERS HAVING SOLUBILITY PARAMETERS OUTSIDE PREFERRED RANGE AND HAVING SIGNIFICANT POLARITY

| Example No. | Additive | Weight Percent Additive | Modifier Solubility Parameter (cal/cc) | Additive Compatible |
|---|---|---|---|---|
| 62 | None | 0 | 9.59 | — |
| 71 | Glycolide | 12.4 | 10.79 | yes |
| 72 | Glycolide | 8.3 | 10.79 | yes |
| 73 | OGA (DP = 2)[a] | 5.6 | ~12.5 | somewhat |
| 74 | OGA (DP = 5)[a] | 18 | ~12.5 | somewhat |
| 75 | OGA (DP = 2)[a] and glycolide | 30 OGA 9 glycolide | ~11.8 | yes |
| 85 | 1-Methyl-2-Pyrrolidone | 30 | 11.3 | yes |
| 86 | N-ethyl o,p-toluene sulfonamide (Santicizer 8) | 20 | 14.39 | yes |
| 87 | Undecanone | 30 | 7.80 | yes |
| 87B | o,p-Toluene sulfonamide | 20 | 16.22 | yes |

[a] Oligomeric glycolic acid with degree of polymerization as shown.

TABLE 18

PHYSICAL PROPERTIES OF 90/10 L-LACTIDE/D,L-LACTIDE COPOLYMER COMPOSITION WITH MODIFIERS OUTSIDE PREFERRED SOLUBILITY PARAMETER RANGE AND HAVING SIGNIFICANT POLARITY

| Example No. | Tensile Yield Strength (1000 psi) | Strain at Yield (Percent) | Elastic Modulus (1000 psi) | Break Strength (1000 psi) | Strain at Break (percent) | Plasticization by Additive |
|---|---|---|---|---|---|---|
| 62 | (a) | (a) | 254. | 8.43 | 4 | — |
| 71 | 1.95 | 5 | 97.3 | 3.65 | 396 | good |
| 72 | 5.80 | 4 | 228. | 3.97 | 225 | good |
| 73 | (a) | (a) | 212. | 4.65 | 3 | <fair |
| 74 | (a) | (a) | 289. | 6.39 | 3 | <fair |
| 75 | (a) | (a) | 177. | 2.90 | 2 | fair |
| 85 | 2.18 | 33 | 99.8 | 2.20 | 89 | good |
| 86 | 0.293 | 47 | 216 | 1.52 | 173 | good |
| 87 | 3.92 | 64 | 229. | 3.95 | 248 | good |

TABLE 18-continued

PHYSICAL PROPERTIES OF 90/10 L-LACTIDE/D,L-LACTIDE COPOLYMER COMPOSITION WITH MODIFIERS OUTSIDE PREFERRED SOLUBILITY PARAMETER RANGE AND HAVING SIGNIFICANT POLARITY

| Example No. | Tensile Yield Strength (1000 psi) | Strain at Yield (Percent) | Elastic Modulus (1000 psi) | Break Strength (1000 psi) | Strain at Break (percent) | Plasticization by Additive |
|---|---|---|---|---|---|---|
| 87B | 0.573 | 16 | 39.0 | 1.32 | 120 | good |

(a) No yield point.

EXAMPLES 88–90

Examples 88–90 illustrate modifiers used with a homopolymer of L-lactide.

In Example 88, L-lactide homopolymer was prepared by methods similar to Example 58. Thus, 500 g of twice recrystallized L-lactide was thoroughly dried, and polymerized using 0.10 g of stannous chloride dihydrate at 180° to 184° C. over 6 hours. The polymer is very hard and stiff, opaque and crystalline. It is difficult to press into defect-free films.

In Examples 89–90, various compounds, as shown in Table 19, were tested as potential modifiers for the polymer of Example 88. The polymer and compounds were blended and mixed at 330° F. on an open, two roll mill. The mixtures were pressed into films for physical property measurements, the results of which are shown in Table 20. Both modifiers plasticized L-PLA, but lactide enhanced strain at break more than the citrate under these test conditions.

EXAMPLE 91

A 90/10 L-lactide/D,L-lactide copolymer was milled-rolled with 10% D,L-lactide at 350° F. The lactide volatilizes considerably, so that at the end of the mixing, an analysis shows only 0.5 to 4% lactide was incorporated. The experiment is repeated except that 35%, DP 2 to 3 oligomeric lactic acid is added at 350° F., then the mill roll temperature is dropped to 300° F. where 10% D,L-lactide is added. Analysis shows the lactide incorporated was 8.7%.

TABLE 19

COMPATIBILITY OF L-LACTIDE HOMOPOLYMER WITH MODIFIERS

| Example No. | Additive | Percent Additive | Solubility Parameter (cal/cc) | Modifier Compatible |
|---|---|---|---|---|
| 88 | None | 0 | 9.59 | — |
| 89 | Lactide | 14 | 10.13 | yes |
| 90 | Acetyl tributyl citrate | 15–30 | 9.0–9.4 | yes |

TABLE 20

PHYSICAL PROPERTIES OF L-LACTIDE HOMOPOLYMER COMPOSITIONS

| Example No. | Tensile Yield Strength (1000 psi) | Strain at Yield (Percent) | Elastic Modulus (1000 psi) | Break Strength (1000 psi) | Strain at Break (percent) | Plasticization by Additive |
|---|---|---|---|---|---|---|
| 88 | (Too brittle to test) | | | | | — |
| 89 | 0.849 | 38 | 60.7 | 2.03 | 192 | yes |
| 90 | 0.785 | 2 | 53.1 | 1.39 | 9 | yes |

What is claimed is:

1. A degradable film material comprising:
   a) a nontoxic hydrolytically degradable polymer comprising repeating monomer or comonomer units selected from the group consisting of:

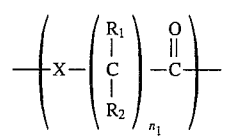

i)

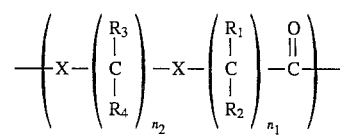

ii)

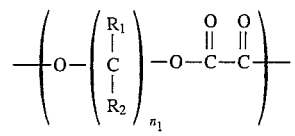

iii)

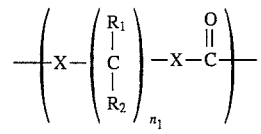

iv)

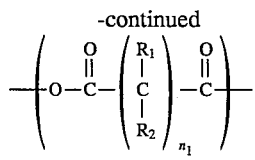

wherein X is the same or different and is O or NR' R' being the same, or different and being H, hydrocarbyl, or substituted hydrocarbyl; $R_1$, $R_2$, $R_3$ $R_4$ can be the same or different and are hydrogen, hydrocarbyl containing 1 to 24 carbon atoms, or substituted hydrocarbyl containing 1 to 24 carbon atoms, and where $n_1$ and $n_2$ can be the same or different and are an integer of from 1–12;

b) a nontoxic modifier, wherein said modifier is compatible with said polymer such that the film material has a uniform appearance and said modifier is nonvolatile and nonfugitive; and c) wherein said film material has a tensile strength of less than about 20,000 psi.

2. The film material of claim 1, wherein said polymer has a weight average molecular weight from about 5,000 to about 1,500,000.

3. The film material of claim 1, wherein said polymer is biodegradable.

4. The film material of claim 1, wherein said polymer comprises repeating monomer or comonomer units selected from the group consisting of:

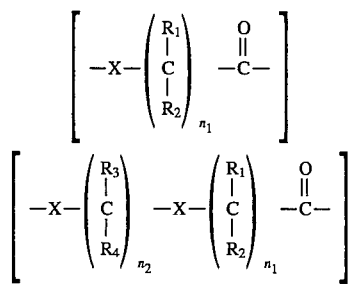

wherein X is the same or different and is O or NR' with R' being the same or different and being H, hydrocarbyl, or substituted hydrocarbyl; $R_1$ and $R_2$ can be the same or different and are hydrogen, hydrocarbyl containing 1 to 24 carbon atoms, or substituted hydrocarbyl containing 1 to 24 carbon atoms, and where $n_1$ and $n_2$ can be the same or different and are an integer of from 1–12.

5. The film material of claim 4, wherein said polymer has a weight average molecular weight from about 100,000 to about 500,000.

6. The film material of claim 4, wherein said repeating monomer or comonomer units comprise repeating monomer or comonomer units derived from monomers selected from the group consisting of alpha-hydroxycarboxylic acids, beta-hydroxycarboxylic acids, gamma-hydroxycarboxylic acids, delta-hydroxycarboxylic acids, epsilon-hydroxycarboxylic acids, beta-lactones, gamma-lactones, delta-lactones, epsilon-lactones, beta-lactams, gamma-lactams, delta-lactams, epsilon-lactams, cyclic diesters of alpha-hydroxycarboxylic acids, dioxanones, substituted variations of the foregoing compounds, and combinations thereof.

7. The film material of claim 4, wherein said repeating units comprise repeating units derived from monomers selected from the group consisting of lactic acid, glycolic acid, epsilon-hydroxycaproic acid, lactide, glycolide, epsilon-caprolactone, delta-valerolactone, substituted variations of the foregoing compounds, and combinations thereof.

8. The film material of claim 4, wherein said polymer is produced by polymerization of monomers, at least 50% by weight of which are monomers selected from the group consisting of lactic acid, lactide, and combinations thereof.

9. The film material of claim 8, wherein said lactide monomers comprise a preponderance of optically active lactide and a lesser amount of optically inactive lactide selected from the group consisting of racemic L,D-lactide and meso L,D-lactide.

10. The film material of claim 4, wherein said polymer is produced by polymerization of monomers, at least 75% of which are monomers selected from the group consisting of lactic acid, lactide and combinations thereof.

11. The film material of claim 1, wherein said polymer does not bioaccumulate.

12. The film material of claim 1, wherein said polymer and modifier are generally regarded as safe.

13. The film material of claim 1, wherein said modifier is intimately dispersible in said polymer, and wherein said polymer is swellable in said modifier.

14. The film material of claim 1, wherein said modifier has a solubility parameter within about 2.0 calories per cubic centimeter of the solubility parameter of said polymer.

15. The film material of claim 1, wherein said modifier has a solubility parameter within about 1.0 calories per cubic centimeter of the solubility parameter of said polymer.

16. The film material of claim 1, wherein said modifier has a solubility parameter within about 0.5 calories per cubic centimeter of the solubility parameter of said polymer.

17. The film material of claim 4, wherein said solubility parameter of said modifier is from about 7.5 to about 16.5 calories per cubic centimeter.

18. The film material of claim 4, wherein said solubility parameter of said modifier is from about 8.0 to about 12.0 calories per cubic centimeter.

19. The film material of claim 4, wherein said polymer has a solubility parameter of from about 9.0 to about 11.0 calories per cubic centimeter.

20. The film material of claim 1, wherein said polymer and modifier have hydrogen bonding indices within about 10 units of each other.

21. The film material of claim 20, wherein said polymer and modifier have hydrogen bonding indices within about 5 units of each other.

22. The film material of claim 1, wherein said polymer and modifier dielectric constants are within about 20 units of each other.

23. The film material of claim 1, wherein said polymer and modifier dielectric constants are within about 5 units of each other.

24. The film material of claim 1, wherein said polymer and modifier have dipole moments within about 6 units of each other.

25. The film material of claim 1, wherein said polymer and modifier have dipole moments within about 2 units of each other.

26. The film material of claim 1, wherein said polymer and modifier have HLB values within about 5 and about 8 HLB units of each other.

27. The film material of claim 1, wherein said polymer and modifier have HLB values within about 3 and about 6 HLB units of each other.

28. The film material of claim 1, wherein said polymer is less than about 20% crystalline.

29. The film material of claim 1, wherein the polymer is a copolymer in which no one monomer constitutes more than about 95 weight percent of the polymer.

30. The film material of claim 1, wherein said modifier has a vapor pressure of less than about 50 Torr at 180° C.

31. The film material of claim 1, wherein said modifier has a boiling temperature above about 280° C. at 1 atmosphere pressure.

32. The film material of claim 1, wherein said modifier is thermally and chemically stable at temperatures below about 130° C.

33. The film material of claim 1, wherein said modifier comprises modifier selected from the group consisting of dicarboxylic acids, derivatives of dicarboxylic acids, polyesters of dicarboxylic acids, tricarboxylic acids, derivatives of tricarboxylic acids, polyesters of tricarboxylic acids, cyclic diesters of alpha-hydroxycarboxylic acids, derivatives of cyclic diesters of alpha-hydroxycarboxylic acids, oligomers of cyclic diesters of alpha-hydroxycarboxylic acids, beta-lactones, delta-lactones, gamma-lactones, ε-lactones, oligomers of alpha-hydroxycarboxylic acids, esters of oligomers of alpha-hydroxycarboxylic acids, benzoic acid derivatives, epoxy derivatives, glycol derivatives, phthalic acid derivatives, phosphoric acid derivatives, ketones, amides, nitriles, and combinations of the foregoing.

34. The film material of claim 33, wherein said modifier comprises modifier selected from the group consisting of adipic acid derivatives, azelaic acid derivatives, cyclic esters of oligomers of lactic acid, esters of oligomers of lactic acid, citric acid derivatives, polyesters of adipic acid, polyesters of azelaic acid, polyesters of sebacic acid, sebacic acid derivatives, benzoic acid derivatives, epoxy derivatives, glycol derivatives, phthalic acid derivatives, phosphoric acid derivatives, and combinations thereof.

35. The film material of claim 33, wherein said modifier comprises modifier selected from the group consisting of di-n-hexyl adipate, bis(2-ethylhexyl)adipate, diisodecyl adipate, bis(2-butoxyethyl) adipate, bis(2-ethylhexyl)azelate, lactide, epsilon-caprolactone, glycolide, delta-valerolactone, oligomeric lactic acid, oligomeric lactic acid ethyl ester, acetylated lactoyllactate ethyl ester, tri-n-butyl citrate, tri-n-butyl acetylcitrate, diethylene glycol dibenzoate, dipropylene glycol dibenzoate, epoxidized soy oil, 2-ethylhexyl epoxy tallate, diethylene glycol dinonanoate, triethylene glycol di(2-ethylbutyrate), pentaerythritol esters, alkoxy sucrose and glucose, acylated sucrose and glucose, alkylated and acylated glycols, starch esters, N-acylated amino acid esters, amide derivatives and oligomers of N-acylated amino acid esters, polyethylene glycol ethers, sulfonamides and derivatives, tri(2-ethylhexyl)phosphate, dimethyl phthalate, diethyl phthalate, butyl 2-ethylhexyl phthalate, bis(2-ethylhexyl)phthalate, dicyclohexyl phthalate, diphenyl phthalate, adipic acid polyester with molecular weight from about 190 to about 6000, azelaic acid polyester with molecular weight from about 232 to about 7500, sebacic acid polyester with molecular weight from about 232 to about 7500, di-n-butyl sebacate, and bis(2-ethylhexyl)sebacate, and combinations thereof.

36. The film material of claim 33, wherein said modifier comprises modifier selected from the group consisting of di-n-hexyl adipate, bis(2-butoxyethyl)adipate, bis(2-ethylhexyl)azelate, lactide, epsilon-caprolactone, glycolide, delta-valerolactone, oligomeric lactic acid, oligomeric lactic acid ethyl ester, tri-n-butyl citrate, tri-n-butyl acetylcitrate, dipropylene glycol dibenzoate, epoxidized soy oil, 2-ethylhexyl epoxy tallate, diethylene glycol dinonanoate, triethylene glycol di(2-ethylbutyrate), butyl 2-ethylhexyl phthalate, bis(2-ethylhexyl)phthalate, dicyclohexyl phthalate, adipic acid polyester with molecular weight from about 190 to about 6000, azelaic acid polyester with molecular weight from about 232 to about 7500, sebacic acid polyester with molecular weight from about 246 to about 8000, di-n-butyl sebacate, and combinations thereof.

37. The film material of claim 1, wherein said modifier comprises modifier selected from the group consisting of dicarboxylic acids, derivatives of dicarboxylic acids, polyesters of dicarboxylic acids, tricarboxylic acids, derivatives of tricarboxylic acids, polyesters of tricarboxylic acids, cyclic diesters of alpha-hydroxycarboxylic acids, derivatives of cyclic diesters of alpha-hydroxycarboxylic acids, oligomers of cyclic diesters of alpha-hydroxycarboxylic acids, beta-lactones, delta-lactones, gamma-lactones, epsilon-lactones, oligomers of alpha-hydroxycarboxylic acids, esters of oligomers of alpha-hydroxycarboxylic acids, and combinations of the foregoing.

38. The film material of claim 1, wherein said modifier comprises modifier selected from the group consisting of adipic acid derivatives, azelaic acid derivatives, cyclic esters, oligomers of lactic acid, esters of oligomers of lactic acid, citric acid derivatives, polyesters of adipic acid, polyesters of azelaic acid, polyesters of sebacic acid, sebacic acid derivatives, and combinations thereof.

39. The film material of claim 1, wherein said modifier comprises modifier selected from the group consisting of di-n-hexyl adipate, lactide, epsilon-caprolactone, glycolide, delta-valerolactone, oligomeric lactic acid, oligomeric lactic acid ethyl ester, tri-n-butyl acetylcitrate, adipic acid polyester with molecular weight from about 190 to about 6000, azelaic acid polyester with molecular weight from about 232 to about 7500, and combinations thereof.

40. The film material of claim 1, wherein said modifier comprises modifiers selected from the group consisting of lactic acid, lactide, oligomers of lactic acid, oligomers of lactide and mixtures thereof, wherein said oligomers of lactic acid and oligomers of lactide are defined by the formula:

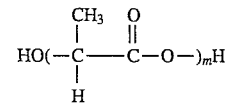

where m is an integer: $2 \leq m \leq 75$.

41. The film material of claim 1, wherein said modifier comprises oligomeric derivatives of lactic acid and lactide selected from the group defined by the formula:

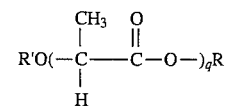

where R=H, alkyl, aryl, alkylaryl or acetyl or acyl, and R is saturated, where R'=H, alkyl, aryl, alkylaryl or acyl, and R' is saturated, where R and R' cannot both be H, where q is an integer: $2 \leq q \leq 75$.

42. The film material of claim 1, wherein said modifier comprises modifiers selected from the group consisting of acetyl tributyl citrate, lactide, glycolide, lactic acid esters, dimethyl adipate, diethyl adipate, caprolactone, acetyl triethyl citrate, bis 2-ethyl hexyl sebacate, and bis 2-ethyl hexyl adipate.

43. The film material of claim 1, wherein said modifier comprises modifiers selected from the group consisting of dibutyl sebacate and triethyl citrate.

44. The film material of claim 1, wherein said polymer is polylactic acid and said modifier is 1-methyl-2-pyrrolidone.

45. The film material of claim 1, wherein said polymer is polylactic acid and said modifier is N-ethyl o,p-toluene sulfonamide.

46. The film material of claim 1, wherein said material comprises between about 1% to about 60% by weight of said modifier.

47. The film material of claim 1, wherein said modifier is hydrolytically degradable.

48. The film material of claim wherein said modifier is biodegradable.

49. The film material of claim 1, wherein said modifier does not bioaccumulate.

50. The film material of claim 1, wherein said modifier is intimately dispersed in said polymer.

51. The film material of claim 1, wherein said film material is a packaging material.

52. The film material of claim 1, wherein said film material is an extruded film.

53. The film material of claim 1, wherein said film material is a blown film.

54. The film material of claim 1, wherein said film material is a compression molded film.

55. The film material of claim 1, wherein said film material has a thickness of less than about 50 mil.

56. The film material of claim 1, wherein said film material has a thickness sufficient to be designated a sheet material.

57. A plasticized polylactic acid film packaging material having a tensile strength of less than about 20,000 psi.

58. A process for producing a degradable film material, comprising:

forming a composition comprising a nontoxic hydrolytically degradable polymer comprising repeating monomer or comonomer units selected from the group consisting of:

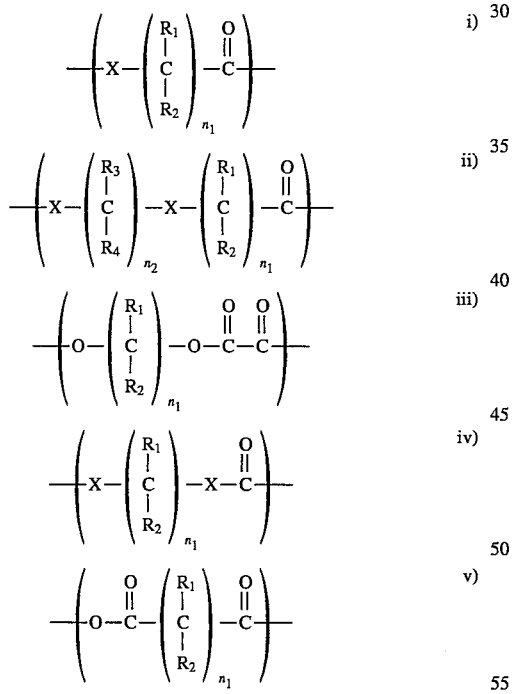

wherein X is the same or different and is O or NR' with R' being the same or different and being H, hydrocarbyl, or substituted hydrocarbyl; $R_1$, $R_2$, $R_3$ and $R_4$ can be the same or different and are hydrogen, hydrocarbyl containing 1 to 24 carbon atoms, or substituted hydrocarbyl containing 1 to 24 carbon atoms, and where $n_1$ and $n_2$ can be the same or different and are an integer of from 1–12, and a nontoxic modifier, wherein said modifier is compatible with said polymer, such that the material has a uniform appearance, into a film having a tensile strength of less than about 20,000 psi under conditions such that said modifier is substantially nonvolatile.

59. A process as claimed in claim 58, wherein less than about 25 percent by weight of said modifier is volatilized during said step of forming.

60. A process as claimed in claim 58, wherein said step of forming comprises compression molding said composition.

61. A process as claimed in claim 58, wherein said step of forming comprises extruding said composition.

62. A process as claimed in claim 58, wherein said film has a thickness of less than about 50 mil.

63. A process as claimed in claim 58, wherein said modifier is substantially nonextractable.

64. A process as claimed in claim 58, wherein said modifier has low extractability.

65. A degradable molded material comprising:

a) a nontoxic hydrolyrically degradable polymer, comprising repeating monomer comonomer units selected from the group consisting of:

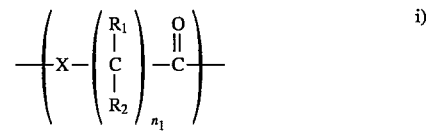

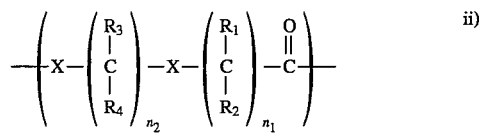

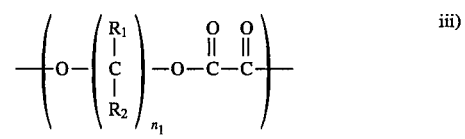

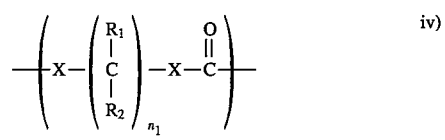

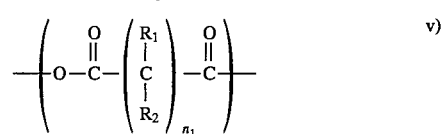

wherein X is the same or different and is O or NR' with R' being the same or different and being H, hydrocarbyl, or substituted hydrocarbyl; $R_1$, $R_2$, $R_3$ and $R_3$ can be the same or different and are hydrogen, hydrocarbyl containing 1 to 24 carbon atoms, or substituted hydrocarbyl containing 1 to 24 carbon atoms, and where $n_1$ and $n_2$ can be the same or different and are an integer of from 1–12;

b) a nontoxic modifier, wherein said modifier is compatible with said polymer such that the material has a uniform appearance and said modifier is nonvolatile and nonfugitive; and c) wherein said material has a tensile strength of less than about 20,000 psi.

66. A degradable foam material comprising:

a) a nontoxic hydrolytically degradable polymer comprising repeating monomer or comonomer units selected from the group consisting of:

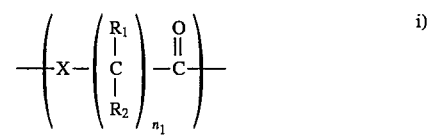

-continued

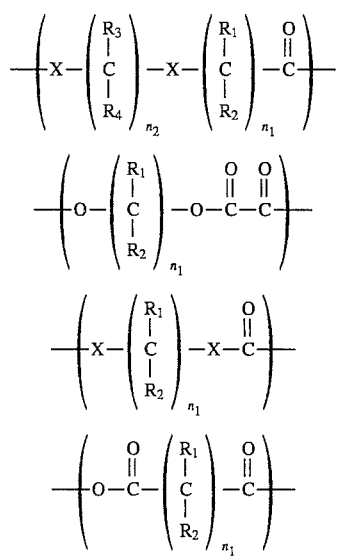

wherein X is the same or different and is O or NR' being the same or different and being H, hydrocarbyl, or substituted hydrocarbyl; $R_1$, $R_2$, $R_3$ and $R_4$ can be the same or different and are hydrogen, hydrocarbyl containing 1 to 24 carbon atoms, or substituted hydrocarbyl containing 1 to 24 carbon atoms, and where $n_1$ and $n_2$ can be the same or different and are an integer of from 1–12;

b) a nontoxic modifier, wherein said modifier is compatible with said polymer such that the material has a uniform appearance and said modifier is nonvolatile and nonfugitive.

67. A degradable spun-bonded nonwoven material comprising:

a) a nontoxic hydrolytically degradable polymer comprising repeating monomer or comonomer units selected from the group consisting of:

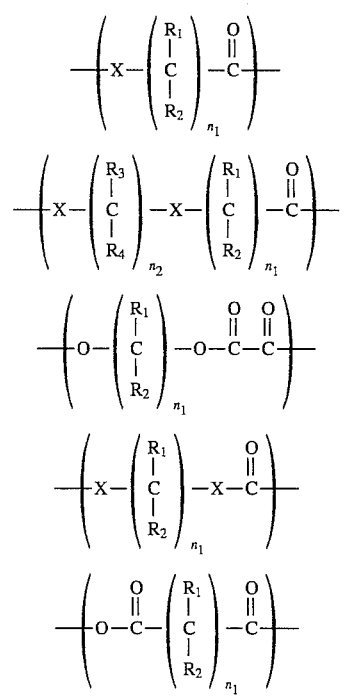

wherein X is the same or different and is O or NR' being the same or different and being H, hydrocarbyl, or substituted hydrocarbyl; $R_1$, $R_2$, $R_3$ and $R_4$ can be the same or different and are hydrogen, hydrocarbyl containing 1 to 24 carbon atoms, or substituted hydrocarbyl containing 1 to 24 carbon atoms, and wherein $n_1$ and $n_2$ can be the same or different and are an integer of from 1–12;

b) a nontoxic modifier, wherein said modifier is compatible with said polymer such that the material has a uniform appearance and said modifier is nonvolatile and nonfugitive.

68. A degradable adhesive material comprising:

a) a nontoxic hydrolytically degradable polymer comprising repeating monomer or comonomer units selected from the group consisting of:

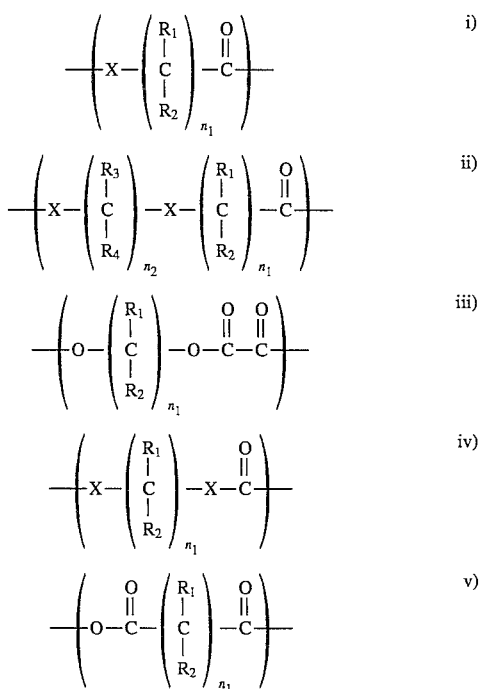

wherein X is the same or different and is O or NR' with R' being the same or different and being H, hydrocarbyl, or substituted hydrocarbyl; $R_1$, $R_2$, $R_3$ and $R_4$ can be the same or different and are hydrogen, hydrocarbyl containing 1 to 24 carbon atoms, or substituted hydrocarbyl containing 1 to 24 carbon atoms, and where $n_1$ and $n_2$ can be the same or different and are an integer of from 1–12;

b) a nontoxic modifier, wherein said modifier is compatible with said polymer such that the material has a uniform appearance and said modifier is nonvolatile and nonfugitive.

69. The film material of claim 8, wherein said lactide monomers comprise a preponderance of optically inactive lactide and a lesser amount of plasticizer to form an amorphous, but orientable, pliable, packaging composition.

70. The film material of claim 52, wherein said film is extruded and oriented.

71. The film material of claim 52, wherein said film is extruded, oriented, and heat-set.

72. The film material of claim 52, wherein said film is extruded, oriented, heat-set, and transparent.

73. The film material of claim 52, wherein said film is extruded and crystalline.

* * * * *